US005843742A

United States Patent [19]
Natsoulis et al.

[11] Patent Number: 5,843,742
[45] Date of Patent: Dec. 1, 1998

[54] ADENO-ASSOCIATED DERIVED VECTOR SYSTEMS FOR GENE DELIVERY AND INTEGRATION INTO TARGET CELLS

[75] Inventors: Georges Natsoulis, Berkeley; Gary Kurtzman, Menlo Park, both of Calif.

[73] Assignee: Avigen Incorporated, Alameda, Calif.

[21] Appl. No.: 525,835

[22] Filed: Sep. 8, 1995

Related U.S. Application Data

[63] Continuation-in-part of Ser. No. 357,503, Dec. 16, 1994, abandoned.

[51] Int. Cl.$^6$ .............................. C12N 15/10; C12N 5/10
[52] U.S. Cl. ..................... 435/172.3; 435/366; 435/367; 435/369
[58] Field of Search .................................. 435/69.1, 69.6, 435/172.1, 172.3, 240.2, 320.1, 325, 366, 367, 369

[56] References Cited

U.S. PATENT DOCUMENTS

| | | | |
|---|---|---|---|
| 4,722,848 | 2/1988 | Paoletti et al. | 424/199.1 |
| 4,965,199 | 10/1990 | Capon et al. | 435/69.6 |
| 5,139,941 | 8/1992 | Muzyczka et al. | 435/172.3 |
| 5,173,414 | 12/1992 | Lebkowski et al. | 435/172.3 |
| 5,219,740 | 6/1993 | Miller et al. | 435/69.6 |
| 5,225,347 | 7/1993 | Goldberg et al. | 435/320.1 |
| 5,399,346 | 3/1995 | Anderson et al. | 424/93.21 |
| 5,436,146 | 7/1995 | Shenk et al. | 435/172.3 |

FOREIGN PATENT DOCUMENTS

| | | |
|---|---|---|
| 0 592 836 A1 | 1/1992 | European Pat. Off. . |
| WO 88/09809 | 12/1988 | WIPO . |
| WO 89/03429 | 4/1989 | WIPO . |
| WO 91/12882 | 9/1991 | WIPO . |
| WO 92/01070 | 1/1992 | WIPO . |
| WO 92/03545 | 3/1992 | WIPO . |
| WO 93/03769 | 3/1993 | WIPO . |
| WO 96/13598 | 5/1996 | WIPO . |
| WO 96/15777 | 5/1996 | WIPO . |

OTHER PUBLICATIONS

McLaughlin et al., J. Virol., vol. 62, No. 6, pp. 1963–1973, Jun. 1988.

Miller and Rosman (1989) "Improved Retroviral Vectors for Gene Transfer and Expression", *BioTechniques* 7:980–990.

Miller, A.D. (1990) "Retrovirus Packaging Cells", *Human Gene–Therapy* 1:5–14.

Scarpa et al. (1991) "Characterization Of Recombinant Helper Retrovirus From Moloney–Based Vectors In Ecotropic And Amphotropic Packaging Lines", *Virology* 180:849–852.

Burns et al. (1993) "Vesicular Stomatitis Virus G Glycoprotein Pseudotyped Retroviral Vectors: Concentration To Very High Titer And Efficient Gene", USA 90:8033–8037.

Boris–Lawrie And Temin (1993) "Recent Advances In Retrovirus Vector Technology", *Cur. Opin. Genet. Develop.* 3:102–109.

Haj–Ahmad and Graham (1986) "Development Of A Helper–Independent Human Adenovirus Vector And Its Use In The Transfer Of The Herpes Simplex Virus Thymidine Kinase Gene", *J. Virol.* 57:267–274.

Bett et al. (1993) "Packaging Capacity And Stabiliy Of Human Adenovirus Type 5 Vectors", *J. Virol.* 67:5911–5921.

Mittereder et al. (1993) "Evaluation Of Efficacy And Safety Of In Vitro, Adenovirus–Mediated Transfer Of The Human Cystic Fibrosis Transmembrane Conductance Regulator cDNA", *Human Gene Therapy* 5:717–729.

Seth et al. (1994) "Mechanism Of Enhancement Of DNA Expression Consequent To Cointernalization Of A Replication–Deficient Adenovirus And Unmodified Plasmid DNA", *J. Virol.* 68:933–940.

Barr et al. (1994) "Efficient Catheter–Mediated Gene Transfer Into the Heart Using Replication–Defective Adenovirus", *Gene Therapy* 1:51–58.

Berkner, K.L. (1988) "Development Of Adenovirus Vectors For The Expression Of Heterologous Genes", *BioTechniques* 6:616–629.

Rich et al. (1993) Development and Analysis Of Recombinant Adenovirus For Gene Therapy Of Cystic Fibrosis, *Human Gene Therapy* 4:461–476.

Berns and Bohenzky (1987) "Adeno–Associated Viruses: An Update", *Advances in Virus Research* (Academic Press, Inc.) 32:243–307.

Muzyczka, N. (1992) "Use of Adeno–Associated Virus As A General Transduction Vector For Mammalian Cells", *Current Topics in Microbiol. and Immunol.* 158:97–129.

Kotin, R.M. (1994) "Prospects for the Use Of Adeno–Associated Virus As A Vector For Human Gene Therapy", *Human Gene Therapy* 5:793–801.

Berns, K.I. "Parvoviridae and Their Replication" in *Fundamental Virology*, 2nd Edition, (B.N. Fields and D.M. Knipe, eds.), pp. 817–837.

Lebkowski et al. (1988) "Adeno–Associated Virus: A Vector System For Efficient Introduction And Intergration Of DNA Into a Variety Of Mammalian Cell Types", *Molec. Cell Biol.* 8:3988–3996.

Vincent et al. (1990) "Replication and Packaging Of HIV Envelope Genes In A Novel Adeno–Associated Virus Vector System", *Vaccines* 90 (Cold Spring Harbor Laboratory Press).

(List continued on next page.)

*Primary Examiner*—David Guzo
*Attorney, Agent, or Firm*—Medlen & Carroll, LLP

[57] ABSTRACT

A novel nucleotide sequence integration and targeting system is described. The system employs adeno-associated virus (AAV) derived vectors which include a selected nucleotide sequence bounded by AAV inverted terminal repeats (ITRs). An AAV rep coding region is also provided, enabling the targeted integration of the selected nucleotide sequence into the genome of a suitable target cell. The nucleotide sequence integration system of the present invention can deliver and integrate large segments of DNA into the genome of target cells. Further, the subject integration system provides the advantage of site-specific integration of the selected nucleotide sequences in a target cell genome, thereby avoiding insertional mutagenesis events experienced with prior systems.

40 Claims, 11 Drawing Sheets

OTHER PUBLICATIONS

Shelling and Smith (1994) "Targeted Integration Of Transfected And Infected Adeno–Associated Virus Vectors Containing The Neomycin Resistance Gene", *Gene Therapy* 1:165–169.

Zhou et al. (1994) "Adeno–Associated Virus 2–Mediated High Efficiency Gene Transfer Into Immature And Mature Subsets Of Hematopoietic Progenitor Cells In Human Umbilical Cord Blood", *J. Exp. Med.* 179:1867–1875.

Mackett, M. et al. "The Contruction And Characterisation Of Vaccine Virus Recombinants Expressing Foreign Genes," in *DNA Cloning: A Practical Approach*, vol. II (D. Glover, ed.) pp. 191–211.

Han et al. (1991) "Inhibition Of Maloney Murine Leukemia Virus–Induced Leukemia In Transgenic Mice Expressing Antisense RNA Commplementary To The Retroviral Packaging Sequences," *Proc. Natl. Acad. Sci. USA* 88:4313–4317.

Uhlmann et al. (1990) "Antisense Oligonucleotides: A New Therapeutic Principle," *Chem. Rev.* 90:543–584.

Helene et al. (1990) "Specific Regulation Of Gene Expression By Antisene, Sense And Antigene Nucleic Acids", *Biochim. Biophys. Acta.* 1049:99–125.

Agarwal et al. (1988) "Oligodeoxynucleoside Phosphoramidates And Phosphorothioates As Inhibitors Of Human Immunodefieciency Virus," *Proc. Natl. Acad. Sci. USA* 85:7079–7083.

Heikkila et al. (1987) "A c–myc Antisense Oligodeoxynucleotide Inhibits Entry Into S Phase But Not Progress From $G_0$ to $G_1$", *Nature* 328–445–449.

Thomson et al. (1994) "Human Herpesvirus 6 (HHV–6) is a Helper Virus for Adeno–Associated Virus Typed 2 (AAV–2) and the AAV–2 rep Gene Homologue in HHV–6 Can Mediate AAV–2 DNA Replication and Regulates Gene Expression", *Virology* 204:304–311.

Graham et al. (1973) "A New Technique For The Assay Of Infectivity Of Human Adenovirus 5 DNA," *Virology,* 52:456.

Chu and Sharp (1981) "SV40 DNA Transfection Of Cells In Suspension: Analysis Of The Efficiency of Transcription And Translation of T–Antigen", *Gene* 13:197.

Edge, (1981) "Total Synthesis Of A Human Leukocyte Interferon Gene", *Nature* 292:756.

Nambiar et al. (1984) "Total Synthesis And Cloning Of a Gene Coding For The Ribonuclease S Protein", *Science* 223:1299.

Jay et al. (1984) "Chemical Synthesis Of A Biologically Active Gene For Human Immune Interferon–γ", *J. Biol. Chem.* 259:6311.

Samulski et al. (1991) "Targeted Intergration Of Adeno–Associated Virus (AAV) Into Human Chromosome 19", *EMBO J.* 10:3941–3950.

Kotin et al. (1992) "Characterization Of A Preferred Site On Human Chromosome 19q For Integration Of Adeno–Associated Virus DNA By Non–Homologous Recombination", *EMBO J.* 11:5071–5078.

Weitzman et al. (1994) "Adeno–Associated Virus (AAV) Rep Proteins Mediate Complex Formation Between AAV DNA And Its Integration Site In Human DNA", *Proc. Natl. Acad. Sci. USA* 91:5808–5812.

Walz and Schlehofer (1992) "Modification Of Some Biological Properties Of HeLa Cells Containing Adeno–Associated Virus DNA Integrated Into Chromosome 17", *J. Virol.* 66:2990–3002.

Hu and Davidson (1987) "The Inducible lac Operator–Repressor System Is Functional In Mammalian Cells", *Cell* 48:555–566.

Urlaub et al. (1980) "Isolation Of Chinese Hamster Cell Mutants Deficient In Dihydrofolate Reductase Activity", *Proc. Natl. Acad. Sci. USA* 77:4216–4220.

Ringold et al. (1981) "Co–Expression And Amplification Of Dihydrofolate Reductase cDNA And The *Escherichia coli* XGPRT Gene In Chinese Hamster Ovary Cells," *J. Mol. and Appl. Genet.* 1:165–175.

McVey et al. (1989) "Properties Of The DNA–Binding Domain Of The Simian Virus 40 Large T Antigen", *Mol. Cell Biol.* 9:5525–5536.

Finney and Bishop (1993) "Predisposition To Neoplastic Transformation Caused by Gene Replacement of H–ras1", *Science* 260:1524–1527.

Trapnell, B.C. (1993) *Advanced Drug Delivery Reviews* 12:185–199.

Michael et al. (1993) "Binding–Incompetent Adenovirus Facilitates Molecular Conjugate–Mediated Gene Transfer By The Receptor–Mediated Endocytosis Pathway", *J. Biol. Chem.* 268:6866–6869.

Wagner et al. (1992) "Coupling of Adenovirus to Transferin–Polylysine/DNA Complexes Greatly Enhances Receptor–Mediated Gene Delivery and Expression of Transfected Genes", *Proc. Natl. Acad. Sci. USA* 89:6099–6103.

Mackett et al. (1984) "General Method For Production And Selection Of Infectious Vaccina Virus Recombinants Expressing Foreign Genes," *J. Virol.* 49:857–864.

Fuerst et al. (1986) "Eukaryotic Transient–Expression System Based On Recombinant Vaccina That Synthesizes Bacteriophage T7 RNA Polymerase," *Proc. Natl. Acad. Sci. USA* 83:8122–8126.

Cech et al. (1992) "RNA Catalysis By A Group I Ribozyme", *J. Biol. Chem.* 267:17479–17482.

O'Gorman et al., (1991) "Recombinase–Mediated Gene Activation And Site–Specific Intergration In Mammalian Cells", *Science* 251:1351–55.

van Deursen et al. (1995) "Cre–Mediated Site–Specific Translocation Between nonhomologous Mouse Chromosomes", *Proc. Natl. Acad Sci. USA* 92:7376–80.

Srivastava et al. (1983) "Nucleotide Sequence And Organization Of The Adeno–Associated Virus 2 Genome", *J. Virol.* 45:555–564.

Samulski et al. (1989) "Helper–Free Stocks Of Recombinant Adeno–Associated Viruses: Normal Intergration Does Not Require Viral Gene Expression", *J. Virol.* 63:3822–3828.

Berns, K. (1990) "Parvovirus Replication", *Microbiol. Rev.* 54(3):316–29.

Ketner et al., (1994) "Efficient Manipulation Of The Human Adenovirus Genome As An Infectious Yeast Artificial Chromosome Clone", *PNAS* 91(3):6186–90.

Cukor, et al., "Biology of Adeno–Associated Virus" In *The Parvoviruses* In The Viruses (H. Fraenkel–Conrat and R.R. Wagner, eds.), Chap. 2, pp. 33–39.

Thomson, et al., (1994) "Human Herpesvirus 6 (HHV–6) is a Helper Virus For Adeno–Associated Vius Type 2 (AAV–2) And The AAV–2 rep Gene Homologue In HHV–6 Can Mediate AAV–2 DNA Replication And Regulate Gene Expression", *Virology* 204:304.

Walz, C. et al., (1992) "Modification Of Some Biological Properties Of HeLa Cells Containing Adeno–Associated Virus DNA Integrated Into Chromosome 17", *J. of Virol.* 2990–3002.

$10^4$ 293 cells transfected with:

p2TRlacZ p2TRlacZ, pGN1764 p2TRlacZ, pRR5 p2TRF8 p2TRF8, pRR5 p2TRF8, pGN1764 p2TRcos p2TRcos, pGN1764 p2TRcos, pRR5

ADENO-ASSOCIATED DERIVED VECTOR SYSTEMS FOR GENE DELIVERY AND INTEGRATION INTO TARGET CELLS

CROSS-REFERENCE TO RELATED APPLICATIONS

This application is a continuation-in-part of U.S. patent application Ser. No. 08/357,503, filed Dec. 16, 1994, now abandoned, from which priority is claimed pursuant to 35 U.S.C. § 120, and which disclosure is hereby incorporated by reference in its entirety.

TECHNICAL FIELD

The present invention relates generally to vectors for gene delivery and integration. More specifically, the invention relates to adeno-associated virus (AAV) derived vector systems for use in gene delivery which provide for integration of a selected nucleotide sequence into a target cell genome.

BACKGROUND OF THE INVENTION

Gene delivery is a promising method for the treatment of acquired and inherited diseases. A number of viral based systems are being developed for gene transfer purposes. In particular, retroviruses are currently the most widely used viral vector system for gene delivery. Retroviral systems generally employ packaging lines which have an integrated defective provirus (the "helper") that expresses all of the genes of the virus but cannot package its own genome due to a deletion of the packaging signal. Thus, the cell line produces empty viral shells. Producer lines can be derived from the packaging lines which, in addition to the helper, contain a viral vector which includes sequences required in cis for replication and packaging of the virus, known as the long terminal repeats (LTRs). The selected gene can be inserted in the vector and packaged in the viral shells synthesized by the retroviral helper. The recombinant virus can then be isolated and delivered to a subject. For descriptions of various retroviral systems, see, e.g., U.S. Pat. No. 5,219,740; Miller and Rosman (1989) *BioTechniques* 7:980–990; Miller, A. D. (1990) *Human Gene Therapy* 1:5–14; Scarpa et al. (1991) *Virology* 180:849–852; Burns et al. (1993) *Proc. Natl. Acad. Sci. USA* 90:8033–8037; and Boris-Lawrie and Temin (1993) *Cur. Opin. Genet. Develop.* 3:102–109.

Despite their popularity, retroviral systems suffer from several drawbacks. In particular, retroviral particles are relatively labile and hence unstable. Therefore, purification of recombinant viruses can lead to significant loss in titer. Furthermore, retroviruses have a limited host range and cannot integrate into nonreplicating cells. Accordingly, cells which do not normally divide, such as mature neurons, or cells which replicate slowly, cannot be genetically altered using retroviral vectors unless stimulated to divide before infection. Additionally, and importantly, retroviruses are known to cause disease in certain animals, including humans, and thus pose a significant health risk to the subject transfected with a recombinant virus. Finally, retrovirus vectors integrate into the host cell chromosome randomly, which may cause insertional mutagenesis by activating oncogenes or inactivating tumor suppressor genes.

Adenovirus based systems have been developed for gene delivery in an attempt to overcome these problems. Human adenoviruses are double-stranded DNA viruses which enter cells by receptor-mediated endocytosis. These viruses are particularly well suited for gene transfer because they are easy to grow and manipulate and they exhibit a broad host range in vivo and in vitro. For example, adenoviruses can infect human cells of hematopoietic, lymphoid and myeloid origin. Furthermore, adenoviruses infect quiescent as well as replicating target cells. Unlike retroviruses which integrate into the host genome, adenoviruses persist extrachromosomally thus minimizing the risks associated with insertional mutagenesis. The virus is easily produced at high titers and is stable so that it can be purified and stored. Even in the replication-competent form, adenoviruses cause only low level morbidity and are not associated with human malignancies. Accordingly, adenovirus vectors have been developed which make use of these advantages. For a description of adenovirus vectors and their uses see, e.g., Haj-Ahmad and Graham (1986) *J. Virol.* 57:267–274; Bett et al. (1993) *J. Virol.* 67:5911–5921; Mittereder et al. (1994) *Human Gene Therapy* 5:717–729; Seth et al. (1994) *J. Virol.* 68:933–940; Barr et al. (1994) *Gene Therapy* 1:51–58; Berkner, K. L. (1988) *BioTechniques* 6:616–629; Rich et al. (1993) *Human Gene Therapy* 4:461–476.

Despite these advantages, adenovirus vectors suffer from several drawbacks. For example, adenovirus vectors express proteins transiently because the transferred gene does not integrate into the chromosome of the target cell. Hence, as the cells divide, the transferred gene is lost. In this regard, such vectors are ineffective for long term gene therapy. Furthermore, adenovirus vectors express viral proteins that may elicit an immune response which may decrease the life of the transduced cell. This immune response may preclude subsequent treatments because of humoral and/or T cell responses.

Still other attempts have been made to perfect gene delivery systems. For example, adeno-associated virus (AAV) systems have also been developed. AAV is a human DNA parvovirus which belongs to the genus Dependovirus. The AAV genome is composed of a linear, single-stranded DNA molecule which contains approximately 4680 bases (Berns and Bohenzky (1987) *Advances in Virus Research* (Academic Press, Inc.) 32:243–307). The genome includes inverted terminal repeats (ITRs) at each end which function in cis as origins of DNA replication and as packaging signals for the virus. The internal nonrepeated portion of the genome includes two large open reading frames, known as the AAV rep and cap regions, respectively. These regions code for the viral proteins involved in replication and packaging of the virion. A family of at least four viral proteins are synthesized from the AAV rep region, Rep 78, Rep 68, Rep 52 and Rep 40, named according to their apparent molecular weight. The AAV cap region encodes at least three proteins, VP1, VP2 and VP3. For a detailed description of the AAV genome, see, e.g., Muzyczka, N. (1992) *Current Topics in Microbiol. and Immunol.* 158:97–129; Kotin, R. M. (1994) Human Gene Therapy 5:793–801; Berns, K. I. "Parvoviridae and their Replication" in *Fundamental Virology*, 2nd Edition, (B. N. Fields and D. M. Knipe, eds.), pages 817–837.

AAV requires coinfection with an unrelated helper virus, such as adenovirus, a herpesvirus or vaccinia, in order for a productive infection to occur. In the absence of such coinfection, AAV establishes a latent state by insertion of its genome into a host cell chromosome. Subsequent infection by a helper virus rescues the integrated copy which can then replicate to produce infectious viral progeny. Unlike the retroviruses, AAV has a wide host range and is able to replicate in cells from any species so long as there is coinfection with a helper virus that will also multiply in that species. Thus, for example, human AAV will replicate in canine cells coinfected with a canine adenovirus. Furthermore, unlike the retroviruses, AAV is not associated with any human or animal disease, does not appear to alter the biological properties of the host cell upon integration and is able to integrate into nondividing cells. It has also recently been found that AAV is capable of site-specific integration into a host cell genome.

In light of the above-described properties, a number of recombinant AAV vectors have been developed for gene delivery. See, e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al. (1988) *Molec. Cell. Biol.* 8:3988–3996; Vincent et al. (1990) *Vaccines* 90 (Cold Spring Harbor Laboratory Press); Carter, B. J. (1992) *Current Opinion in Biotechnology* 3:533–539; Muzyczka, N. (1992) *Current Topics in Microbiol. and Immunol.* 158:97–129; Kotin, R. M. (1994) *Human Gene Therapy* 5:793–801; Shelling and Smith (1994) *Gene Therapy* 1:165–169; and Zhou et al. (1994) *J Exp. Med.* 179:1867–1875.

Recombinant AAV virions can be produced in a suitable host cell which has been transfected with both an AAV helper plasmid and an AAV vector. An AAV helper plasmid generally includes AAV rep and cap coding regions, but lacks AAV ITRs. Accordingly, the helper plasmid can neither replicate nor package itself. An AAV vector generally includes a selected gene of interest bounded by AAV ITRs which provide for viral replication and packaging functions. Both the helper plasmid and the AAV vector bearing the selected gene are introduced into a suitable host cell by transient transfection. The transfected cell is then infected with a helper virus, such as an adenovirus, which transactivates the AAV promoters present on the helper plasmid that direct the transcription and translation of AAV rep and cap regions. Recombinant AAV virions harboring the selected gene are formed and can be purified from the preparation. However, integration, when it occurs, does not appear to be site specific.

Although such recombinant AAV virions have proven useful for introducing several small gene sequences into host cells, gene delivery systems based on those particles are limited by the relatively small size of AAV particles. More particularly, due to the size of the wild-type AAV genome, gene sequences of interest that are larger than about 5 Kb cannot be successfully packaged into AAV virions. This feature greatly reduces the range of gene delivery protocols that can be practiced using AAV virions.

Based upon the discussion presented above, it should be evident that current gene delivery methods are suboptimal. Accordingly, it would be useful to provide nucleotide sequence integration systems that are capable of the site-specific integration features provided by AAV virions, yet are not limited in the size of the nucleotide sequence that can be integrated. In this manner, large DNA molecules can be inserted into suitable target cells without the concomitant risk of insertional mutagenesis due to random integration events such as have been experienced with various prior systems. Until the present invention, this unique set of features has not been provided in gene integration systems.

SUMMARY OF THE INVENTION

The present invention provides for novel systems for gene integration. In particular, AAV derived vector systems are described which allow for the integration of a selected nucleotide sequence into a recipient cell genome. Integration can be targeted to a defined and benign genomic site, thereby eliminating the risk of insertional mutagenesis which can occur with viruses which integrate randomly. The selected nucleotide sequence is not limited by size as in previous systems, since the AAV derived vector systems are not packaged in AAV virions.

The vectors can be provided in recombinant molecules, including a plasmid or a virus. For example, the vectors can be provided in recombinant adenoviruses, thereby combining the advantages of prior adenovirus and AAV gene delivery systems while avoiding their limitations. The system has a broad host range and can be used to infect quiescent as well as replicating target cells. Recombinant viruses can be produced at high titers and are stable so that they can be purified and stored. Furthermore, the system is safe and does not cause human diseases or cancers.

Accordingly, in one embodiment, the invention is directed to a method of integrating a selected nucleotide sequence into the genome of a mammalian cell, comprising: (a) providing: (i) a first nucleic acid construct comprising a nucleotide sequence flanked by a 5' and a 3' adeno-associated virus inverted terminal repeat, and (ii) a second nucleic acid construct having a rep coding region operably linked to control elements capable of directing the transcription and translation of the rep coding region in the mammalian cell; (b) expressing the rep coding region of the second nucleic acid construct, thereby producing an amount of rep expression product capable of facilitating the integration of the nucleotide sequence of the first nucleic acid construct; and (c) integrating the nucleotide sequence of the first nucleic acid construct into the mammalian cell, the integration being facilitated by the rep expression product. In a further embodiment, the invention contemplates a mammalian cell containing the same nucleic acid constructs.

In another embodiment, the invention contemplates a method of integrating a selected nucleotide sequence into the genome of a mammalian cell, comprising: (a) providing: (i) a first nucleic acid construct comprising a nucleotide sequence flanked by a 5' and a 3' adeno-associated virus inverted terminal repeat, and (ii) an amount of rep expression product capable of facilitating the integration of the nucleotide sequence of the first nucleic acid construct; and (b) integrating the nucleotide sequence of the first nucleic acid construct into the mammalian cell, the integration being facilitated by the rep expression product. Moreover, a further embodiment of the present invention contemplates a mammalian cell containing the same nucleic acid constructs.

In some embodiments, the first nucleic acid construct is a recombinant adeno-associated virus vector. In further embodiments, the recombinant adeno-associated virus vector is a plasmid; the mammalian cell is transfected with the plasmid in particular embodiments.

In particular embodiments, the first nucleic acid construct and the second nucleic acid construct are present on the same vector. Conversely, the first nucleic acid construct and the second nucleic acid construct are present on different vectors in other embodiments.

Moreover, the invention contemplates a nucleotide sequence of the first nucleic acid construct that is integrated into chromosome 19q of the mammalian cell. In some embodiments, the nucleotide sequence of the first nucleic acid construct is more than 5,000 base pairs, while it is more than 10,000 base pairs in other embodiments.

In further embodiments, the nucleotide sequence of the first nucleic acid construct encodes a polypeptide. The polypeptide encodes at least a portion of the factor VIII gene in some embodiments. That is, the present invention is not limited to a particular sequence encoding a protein that retains factor VIII activity.

The invention is directed to recombinant DNA molecules, and preferably to plasmids, comprising the nucleic acid constructs disclosed above. In some embodiments, the invention is directed to a recombinant virus comprising the above-described nucleic acid constructs, as well as to target cells infected with the recombinant virus. In one particular embodiment, the virus is a recombinant adenovirus.

In yet additional embodiments, the invention is directed to a method of treating an acquired or inherited disease in a subject, comprising transfecting or infecting a selected target cell from the subject with a plasmid or recombinant virus, respectively comprising the nucleic acid constructs as described above.

These and other embodiments of the subject invention will readily occur to those of ordinary skill in the art in view of the disclosure herein.

DETAILED DESCRIPTION OF THE INVENTION

Figure 1:
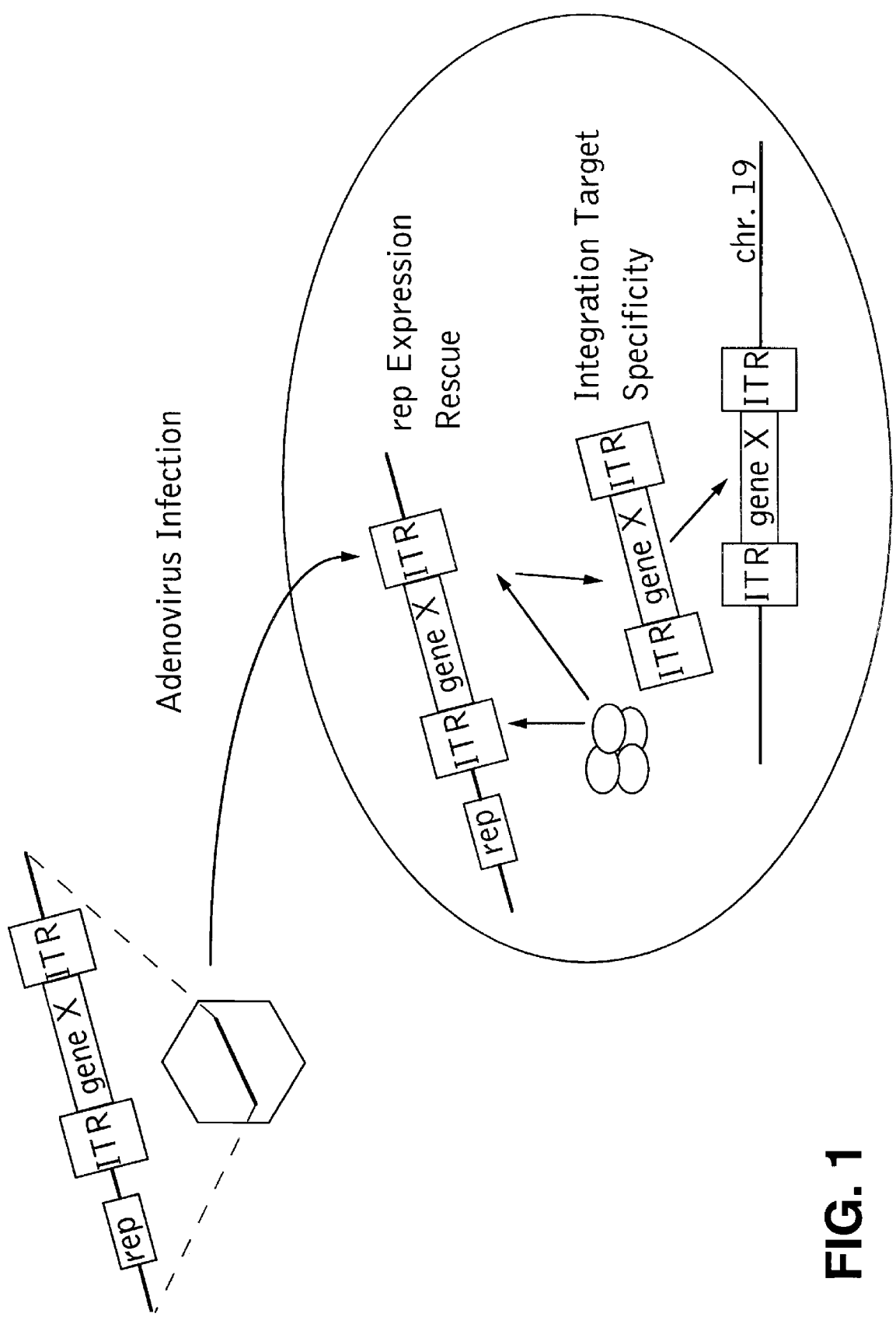
FIG. 1 is a depiction of one embodiment of the subject invention wherein a recombinant adenovirus which includes a nucleic acid construct comprising a rep coding region and a selected nucleotide sequence bounded by AAV ITRs, is used to infect a target cell. The presence of both the rep protein and the AAV ITRs serve to cause targeted integration of the selected nucleotide sequence into chromosome 19 of the target cell.

The practice of the present invention will employ, unless otherwise indicated, conventional methods of virology, microbiology, molecular biology and recombinant DNA techniques within the skill of the art. Such techniques are explained fully in the literature. See, e.g. , Sambrook, et al. *Molecular Cloning: A Laboratory Manual* (Current Edition); *DNA Cloning: A Practical Approach,* vol. I & II (D. Glover, ed.); *Oligonucleotide Synthesis* (N. Gait, ed., Current Edition); *Nucleic Acid Hybridization* (B. Hames & S. Higgins, eds., Current Edition); *Transcription and Translation* (B. Hames & S. Higgins, eds., Current Edition); *CRC Handbook of Parvoviruses,* vol. I & II (P. Tijessen, ed.); *Fundamental Virology,* 2nd Edition, vol. I & II (B. N. Fields and D. M. Knipe, eds.)

All publications, patents and patent applications cited herein, whether supra or infra, are hereby incorporated by reference in their entirety.

As used in this specification and the appended claims, the singular forms "a," "an" and "the" include plural references unless the content clearly dictates otherwise.

A. Definitions

In describing the present invention, the following terms will be employed, and are intended to be defined as indicated below. "Gene transfer" or "gene delivery" refers to methods or systems for reliably inserting a particular nucleotide sequence (e.g., DNA) into targeted cells. Such methods preferably result in the integration of the transferred genetic material into the genome of target cells. Gene transfer provides a unique approach for the treatment of acquired and inherited diseases, and a number of systems have been developed in the art for gene transfer into mammalian cells. See, e.g., U.S. Pat. No. 5,399,346.

By "adeno-associated virus inverted terminal repeats" or "AAV ITRs" is meant the art-recognized palindromic regions found at each end of the AAV genome which function together in cis as origins of DNA replication and as packaging signals for the virus. For use with the present invention, flanking AAV ITRs are positioned 5' and 3' of one or more selected heterologous nucleotide sequences and, together with the rep coding region or the Rep expression product, provide for the integration of the selected sequences into the genome of a target cell.

The nucleotide sequences of AAV ITR regions are known. See, e.g., Kotin, R. M. (1994) *Human Gene Therapy* 5:793–801; Berns, K. I. "Parvoviridae and their Replication" in *Fundamental Virology,* 2nd Edition, (B. N. Fields and D. M. Knipe, eds.) for the AAV-2 sequence. As used herein, an "AAV ITR" need not have the wild-type nucleotide sequence depicted, but may be altered, e.g., by the insertion, deletion or substitution of nucleotides. Additionally, the AAV ITR may be derived from any of several AAV serotypes, including without limitation, AAV-1, AAV-2, AAV-3, AAV-4, AAV-5, AAVX7, etc. The 5' and 3' ITRs which flank a selected heterologous nucleotide sequence need not necessarily be identical or derived from the same AAV serotype or isolate, so long as they function as intended, i.e., to allow for the integration of the associated heterologous sequence into the target cell genome when the rep gene is present (either on the same or on a different vector), or when the Rep expression product is present in the target cell.

By "vector" is meant any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

By an "AAV vector" is meant a vector derived from an adeno-associated virus serotype, including without limitation, AAV-1, AAV-2, AAV-3, AAV-4, AAV-5, AAVX7, etc. AAV vectors can have one or more of the AAV wild-type genes deleted in whole or part, preferably the rep and/or cap genes, but retain functional flanking ITR sequences.

AAV vectors can be constructed using recombinant techniques that are known in the art to include one or more heterologous nucleotide sequences flanked on both ends (5' and 3') with functional AAV ITRs. In the practice of the invention, an AAV vector can include at least one AAV ITR and a suitable promoter sequence positioned upstream of the heterologous nucleotide sequence and at least one AAV ITR positioned downstream of the heterologous sequence. A "recombinant AAV vector plasmid" refers to one type of recombinant AAV ector wherein the vector comprises a plasmid. As with AAV vectors in general, 5' and 3' ITRs flank the selected heterologous nucleotide sequence.

AAV vectors can also include transcription sequences such as polyadenylation sites, as well as selectable markers or reporter genes, enhancer sequences, and other control elements which allow for the induction of transcription. Such control elements are described more fully below.

As used herein, the term "AAV virion" refers to a complete virus particle. An AAV virion may be a wild type AAV virus particle (comprising a linear, single-stranded AAV nucleic acid genome associated with an AAV capsid, i.e., a protein coat), or a recombinant AAV virus particle (described below). In this regard, single-stranded AAV nucleic acid molecules (either the sense/coding strand or the antisense/anticoding strand as those terms are generally defined) can be packaged into an AAV virion; both the sense and the antisense strands are equally infectious.

As used herein, the term "recombinant AAV virion" or "rAAV" is defined as an infectious, replication-defective virus composed of an AAV protein shell encapsidating (i.e., surrounding with a protein coat) a heterologous nucleotide sequence, which in turn is flanked 5' and 3' by AAV ITRs. A number of techniques for constructing recombinant AAV virions are known in the art. See, e.g., U.S. Pat. No. 5,173,414; International Publication Numbers WO 92/01070 (published 23 Jan. 1992) and WO 93/03769 (published 4 Mar. 1993); Lebkowski et al. (1988) *Molec. Cell. Biol.* 8:3988–3996; Vincent et al. (1990) Vaccines 90 (Cold Spring Harbor Laboratory Press); Carter, B.J. (1992) *Current Opinion in Biotechnology* 3:533–539; Muzyczka, N. (1992) *Current Topics in Microbiol. and Immunol.* 158:97–129; Kotin, R. M. (1994) *Human Gene Therapy* 5:793–801; Shelling and Smith (1994) *Gene Therapy* 1:165–169; and Zhou et al. (1994) *J. Exp. Med.* 179:1867–1875.

Suitable nucleotide sequences for use in AAV vectors include any functionally relevant nucleotide sequence. Thus, the AAV vectors of the present invention can comprise any desired gene that encodes a protein that is defective or missing from a target cell genome or that encodes a non-native protein having a desired biological or therapeutic effect (e.g., an antiviral function), or the sequence can correspond to a molecule having an antisense or ribozyme function. Suitable genes include those used for the treatment of inflammatory diseases, autoimmune, chronic and infectious diseases, including such disorders as AIDS, cancer, neurological diseases, cardiovascular disease, hypercholestemia; various blood disorders including various anemias, thalassemias and hemophilia; genetic defects such as cystic fibrosis, Gaucher's Disease, adenosine deaminase (ADA) deficiency, emphysema, etc. A number of antisense oligonucleotides (e.g., short oligonucleotides complementary to sequences around the translational initiation site (AUG codon) of an MRNA) that are useful in antisense therapy for cancer and for viral diseases have been described in the art. See, e.g., Han et al. (1991) *Proc. Natl. Acad. Sci. USA* 88:4313–4317; Uhlmann et al. (1990) *Chem. Rev.* 90:543–584; Helene et al. (1990) *Biochim. Biophys. Acta.* 1049:99–125; Agarwal et al. (1988) *Proc. Natl. Acad. Sci. USA* 85:7079–7083; and Heikkila et al. (1987) *Nature* 328:445–449. For a discussion of suitable ribozymes, see, e.g., Cech et al. (1992) *J. Biol. Chem.* 267:17479–17482 and U.S. Pat. No. 5,225,347 to Goldberg et al.

By "recombinant virus" is meant a virus that has been genetically altered, e.g., by the addition or insertion of a heterologous nucleic acid construct into the particle.

As used herein, the terms facilitate, facilitation, and the like refer broadly to making an action or result more easily achieved. For example, the expression product of the rep gene is required to target selected nucleotide sequences into a cell's genome. The term includes, but is not limited to, site specific integration of nucleotide sequences into chromosome 19.

By "AAV rep coding region" is meant the art-recognized region of the AAV genome which encodes the replication proteins of the virus which are collectively required for replicating the viral genome, or functional homologues thereof such as the human herpesvirus 6 (HHV-6) rep gene which is also known to mediate AAV-2 DNA replication (Thomson et al. (1994) *Virology* 204:304–311). Thus, the rep coding region includes at least the genes encoding for AAV Rep 78 and Rep 68 (the "long forms of Rep"), and Rep 52 and Rep 40 (the "short forms of Rep"), or functional homologues thereof. For a further description of the AAV rep coding region, see, e.g., Muzyczka, N. (1992) *Current Topics in Microbiol. and Immunol.* 158:97–129; and Kotin, R. M. (1994) *Human Gene Therapy* 5:793–801. The rep coding region, as used herein, can be derived from any viral serotype, such as the AAV serotypes described above. The region need not include all of the wild-type genes but may be altered, (e.g., by insertion, deletion or substitution of nucleotides), so long as the rep genes present provide for sufficient integration functions when expressed in a suitable target cell. "Rep expression products" are defined herein to include both the short forms and the long forms of AAV Rep, including functional homologous thereof.

The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) *Virology*, 52:456, Sambrook et al. (1989) *Molecular Cloning, a laboratory manual,* Cold Spring Harbor Laboratories, New York, Davis et al. (1986) *Basic Methods in Molecular Biology,* Elsevier, and Chu et al. (1981) *Gene* 13:197. Such techniques can be used to introduce one or more exogenous DNA moieties, such as an AAV vector, AAV helper constructs, and other nucleic acid molecules, into suitable host cells.

As used herein, a "nucleotide sequence integration system" intends the operative combination of: (1) a first nucleic acid construct comprising a nucleotide sequence of interest flanked by a 5' and a 3' AAV ITR; and (2) either a further nucleic acid construct having a rep coding region operably linked to control elements capable of directing the transcription and translation of the rep coding region in a suitable target cell, or a suitable amount of Rep expression products, whereby the nucleotide integration system provides for the integration of the nucleotide sequence of interest from the first construct into the genome of a target cell that has been transfected with said integration system.

By "target cell," or "target mammalian cell" is meant a cell which has been transformed, or is capable of transformation, by a nucleic acid construct or an AAV vector bearing a selected nucleotide sequence of interest. The term includes the progeny of the parent cell, whether or not the progeny is identical in morphology or in genetic make-up to the original parent, so long as the selected nucleotide sequence is present.

A cell has been "stably transformed" with a nucleic acid construct comprising a selected nucleotide sequence of interest when the construct has been introduced inside the cell membrane and the sequence of interest has been integrated into the target cell genome such that the integrated nucleotide sequence is capable of being inherited by daughter cells through chromosome replication. The cell can be transformed using any of several techniques, including transduction, transfection and infection. Stability is demonstrated by the ability of the target cell to establish cell lines or clones comprised of a population of daughter cells which contain the nucleotide sequence of interest.

The term "heterologous" as it relates to nucleic acid sequences such as coding sequences and control sequences, denotes sequences that are not normally joined together, and/or are not normally associated with a particular cell. Thus, a "heterologous" region of a nucleic acid construct or an AAV vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention. Allelic variation or naturally occurring mutational events do not give rise to heterologous DNA, as used herein.

A "coding sequence" or a sequence which "encodes" a particular protein, is a nucleic acid sequence which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from procaryotic or eucaryotic MRNA, genomic DNA sequences from procaryotic or eucaryotic DNA, and even synthetic DNA sequences. A transcription termination sequence will usually be located 3' to the coding sequence.

A "nucleic acid" sequence refers to a DNA or RNA sequence. The term captures sequences that include any of the known base analogs of DNA and RNA such as, but not limited to 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5' -methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The terms DNA "control sequences" and "control elements" refer collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences/elements need always be present so long as the selected coding sequence is capable of being replicated, transcribed and translated in an appropriate host cell.

"Operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

"Homology" refers to the percent of identity between two polynucleotide or two polypeptide moieties. The correspondence between the sequence from one moiety to another can be determined by techniques known in the art. For example, homology can be determined by a direct comparison of the sequence information between two polypeptide molecules by aligning the sequence information and using readily available computer programs. Alternatively, homology can be determined by hybridization of polynucleotides under conditions which form stable duplexes between homologous regions, followed by digestion with single-stranded-specific nuclease(s), and size determination of the digested fragments. Two DNA, or two polypeptide sequences are "substantially homologous" to each other when at least about 80%, preferably at least about 90%, and most preferably at least about 95% of the nucleotides or amino acids match over a defined length of the molecules, as determined using the methods above.

A "functional homologue," or a "functional equivalent" of a given polypeptide includes molecules derived from the native polypeptide sequence, as well as recombinantly produced or chemically synthesized polypeptides which function in a manner similar to the reference molecule to achieve a desired result. Thus, a functional homologue of AAV Rep expression products (e.g., Rep 78, Rep 68, Rep 52 and Rep 40) encompasses derivatives and analogues of those polypeptides—including any single or multiple amino acid additions, substitutions and/or deletions occurring internally or at the amino or carboxy termini thereof, so long as replication activity remains.

B. General Methods

Central to the present invention is the development of a nucleotide sequence integration system which allows for the efficient targeting and integration of a selected nucleotide sequence into the genome of a target mammalian cell. A particular feature of the invention is that such integration can be directed to non-essential regions of particular chromosomes of the target cell, thereby avoiding the risk of insertional mutagenesis which can occur with random integration of a viral vector.

More particularly, the present invention makes use of a DNA vector comprising a first nucleic acid construct bearing a selected nucleotide sequence. The selected sequence is flanked on the 5' and 3' ends with AAV ITRs. Also present, on either the same or a different vector, is a second nucleic acid construct which includes a rep coding region, with the proviso that if the rep coding region and the selected nucleotide sequence are present on the same vector, the rep coding region lies outside of the ITRs so that it will not be integrated along with the selected nucleotide sequence. Furthermore, when present on the same vector, the rep coding region can be positioned either upstream or downstream of the selected nucleotide sequence. A particular embodiment of the subject invention, wherein the rep coding region and the selected nucleotide sequence are found on the same DNA vector, is shown in FIG. 1.

The first and second nucleic acid constructs can be engineered using recombinant techniques known to those of skill in the art. In particular, the first nucleic acid construct which harbors the nucleotide sequence of interest bounded by the AAV ITRs, can be constructed by directly inserting a selected sequence into an AAV genome which has the rep and cap coding regions excised, e.g. using restriction enzymes. Other portions of the AAV genome can also be deleted, so long as a sufficient portion of the ITRs remain to allow for integration functions. Such constructs can be designed using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al. (1988) *Molec. Cell. Biol.* 8:3988–3996; Vincent et al. (1990) Vaccines 90 (Cold Spring Harbor Laboratory Press); Carter, B. J. (1992) *Current Opinion in Biotechnology* 3:533–539; Muzyczka, N. (1992) *Current Topics in Microbiol. and Immunol.* 158:97–129; Kotin, R. M. (1994) *Human Gene Therapy* 5:793–801; Shelling and Smith (1994) *Gene Therapy* 1:165–169; and Zhou et al. (1994) *J. Exp. Med.* 179:1867–1875.

Alternatively, the AAV ITRs can be excised from the viral genome or from an AAV vector containing the same and fused 5' and 3' of the selected nucleotide sequence which is present in another vector, using standard ligation techniques, such as those described in Sambrook et al., supra. For example, ligations can be accomplished in 20 mM Tris-Cl pH 7.5, 10 mM $MgCl_2$, 10 mM DTT, 33 ug/ml BSA, 10 mM-50 mM NaCl, and either 40 mM ATP, 0.01–0.02 (Weiss) units T4 DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 30–100 $\mu$g/ml total DNA concentrations (5–100 nM total end concentration). AAV vectors which contain ITRs have been described in, e.g., U.S. Pat. No. 5,139,941. In particular, several AAV vectors are described therein which are available from the American Type Culture Collection ("ATCC") under accession numbers 53222, 53223, 53224, 53225 and 53226.

Additionally, chimeric genes can be produced synthetically which include the AAV ITR sequences fused 5' and 3' of the selected nucleotide sequence. AAV ITR nucleotide sequences are known. See, e.g., Kotin, R. M. (1994) *Human Gene Therapy* 5:793–801; and Berns, K. I. "Parvoviridae and their Replication" in *Fundamental Virology*, 2nd Edition, (B. N. Fields and D. M. Knipe, eds.), for the AAV-2 sequence. Preferred codons for expression of the chimeric nucleotide sequence in mammalian cells can be used. The complete chimeric sequence is assembled from overlapping oligonucleotides prepared by standard methods. See, e.g., Edge, *Nature* (1981) 292:756; Narnbair et al. Science (1984) 223:1299; Jay et al. *J. Biol. Chem.* (1984) 259:6311.

The selected nucleotide sequence of the first nucleic acid construct can comprise any desired gene that encodes a protein that is defective or missing from a recipient cell genome or that encodes a non-native protein having a desired biological or therapeutic effect (e.g., an antiviral function), or the sequence can correspond to a molecule having an antisense or ribozyme function. Suitable genes include those used for the treatment of inflammatory diseases, autoimmune, chronic and infectious diseases, including such disorders as AIDS, cancer, neurological diseases, cardiovascular disease, hypercholestemia; various blood disorders including various anemias, thalassemias and hemophilia; genetic defects such as cystic fibrosis, Gaucher's Disease, adenosine deaminase (ADA) deficiency, emphysema, etc.

As explained above, a second nucleic acid construct is also provided which includes a rep coding region. The presence of rep provides for targeted insertion of the selected nucleotide sequence (from the first nucleic acid construct) into non-essential regions of particular chromosomes. More particularly, Rep expression products are thought to mediate integration events which take place between compatible AAV ITR sequences and sequences present in a target cell genome. In this regard, it has been shown that the integration locus for AAV (termed "AAVS 1") is human chromosome 19q13.3-qter. Samulski et al. (1991) *EMBO J.* 10:3941–3950; Kotin et al. (1992) *EMBO J.* 11:5071–5078. AAV vectors including the AAV rep coding region positioned between the ITRs have been shown to integrate into AAVS 1 of chromosome 19. Shelling and Smith (1994) *Gene Therapy* 1:165–169. Rep recognition sequences have also been identified on human chromosome 19 near sites of viral integration in AAVS1. Weitzman et al. (1994) *Proc. Natl. Acad. Sci. USA* 91:5808–5812. AAV constructs have also been shown to integrate into chromosome 17. Walz and Schlehofer (1992) *J. Virol* 66:2990–3002.

The rep coding region can be obtained from the viral genome or from a vector known to include the same. In this regard, a number of rep containing AAV vectors are known, including the several vectors described in, e.g., U.S. Pat. No. 5,139,941, having ATCC accession numbers 53222, 53223, 53224, 53225 and 53226. Similarly, methods of obtaining the HHV-6 homologue of AAV rep are described in Thomson et al. (1994) *Virology* 204:304–311.

The rep coding region will be operably linked to control sequences that direct the transcription and translation thereof. Such control elements include one or more of promoters, polyadenylation signals, transcription termination sequences, upstream regulatory domains, replication sequences, enhancers, and the like, which collectively provide for the transcription and translation of the rep coding region when present in the target cell.

Useful promoter sequences include those derived from sequences encoding mammalian viral genes. Examples include but are not limited to the homologous AAV promoters, the SV40 early promoter, mouse mammary tumor virus LTR promoter; adenovirus major late promoter (Ad MLP); a herpes simplex virus (HSV) promoter, a cytomegalovirus (CMV) promoter, a rous sarcoma virus (RSV) promoter, synthetic promoters, hybrid promoters, and the like. In addition, sequences derived from nonviral genes, such as the murine metallothionein gene, will also find use herein. Such promoter sequences are commercially available from, e.g., Stratagene.

Additionally, regulatory elements can be picked that allow for the controlled expression of the rep coding region in the target cell. Such elements are turned on in response to an appropriate effector. In this way, the Rep proteins can be made when integration of the desired nucleotide sequence into the genome of the target cell is desired. Regulatory sequences are known to those of skill in the art, and include e.g., elements derived from the lac operator-repressor system (see, e.g., Hu and Davidson *Cell* (1987) 48:555–566), origins of replication including those derived from papovaviruses, such as the SV40 origin of replication (SV40Ori) for which the T antigen is the effector, as well as cellular origins of replication, such as the dihydrofolate reductase (dhfr) gene for which methotrexate is the effector. See, e.g. Urlaub et al. (1980) *Proc. Natl. Acad. Sci. USA* 77:4216–4220; Rungold et al. (1981) *J. Mol. and Appl. Genet.* 1:165–175.

For these methods, the appropriate effector will be available in the target cell at the time that expression of the AAV rep coding region is desired. Systems for administering regulatory compounds are known in the art. See, e.g., International Publication No. WO 88/09809, McVey et al. (1989) *Mol. Cell. Biol.* 9:5525–5536; and Van Doren et al. (1984) *Mol. Cell. Biol.* 9:5525–5536.

The second nucleic acid construct which includes the AAV rep coding region may also include selectable markers, such as genes which confer antibiotic resistance or sensitivity, or impart color, or change the antigenic characteristics, when the transformed cells are grown in an appropriate selective medium.

Once engineered, the constructs can be used directly to transform a selected target cell. In this regard, the cell to be transformed will depend on the purpose for gene transfer, e.g., the disease state being treated. For example, the system of the present invention can be used to deliver and integrate nucleotide sequences into any nucleated cell including stem, progenitor and erythroid cells; as well as any of the various white blood cells such as lymphocytes, neutrophils, eosinophils, basophils, monocytes; tissue specific cells, such as those derived from lung, heart, kidney, liver, spleen, pancreatic tissue, connective tissue, muscle and bone tissue including osteocytes, gangliocytes, epithelial and endothelial cells, ependymal cells, reticuloendothelial cells, dendritic and neural cells, and the like.

Generally, target cells will be transformed with the nucleotide sequence integration system of the present invention either in vivo or ex vivo. If transformed ex vivo, the desired target cell type will be removed from the subject, transformed and reintroduced into the subject. In this regard, a number of methods are known in the art for transforming cells, including dextran-mediated transfection, calcium phosphate precipitation, polybrene-mediated transfection, protoplast fusion, electroporation, encapsulation of the nucleic acid constructs in liposomes, and direct microinjection of the DNA into nuclei. Such systems are known in the art and have been described in e.g., Finney and Bishop (1993) *Science* 260:1524–1527. The transformed cells can be screened for those cells harboring the selected gene, using conventional techniques such as Southern blots and/or PCR.

If delivered in vivo, the nucleic acid constructs will be formulated into pharmaceutical compositions and will generally be administered parenterally, e.g., by injection. Additional formulations suitable for other modes of administration include oral and pulmonary formulations, suppositories, and transdermal applications. Dosage treatment may be a single dose schedule or a multiple dose schedule. One of skill in the art can readily determine an appropriate dosage using standard dose response curves.

Alternatively, recombinant viruses can be used to deliver the constructs of the present invention to the target cell. In particular, the present invention has been exemplified using an adenovirus as the delivery system, as depicted in FIG. 1. However, any recombinant virus which is capable of infecting the target cell of interest, will find use in the present system. In this regard the nucleic acid constructs will first be used to transform a selected virus and the transformed virus, in turn, used to deliver a selected nucleotide sequence to a suitable target cell.

If adenoviruses are used, any of the various human adenovirus strains, such as but not limited to, adenovirus type 2 (Ad2), adenovirus type 5 (Ad5), adenovirus type 7 (Ad7), adenovirus type 12 (Ad12), will find use herein. Other adenoviruses which will also be useful with the present invention include mutant adenoviruses which have been manipulated, such as by the removal of nonessential regions of the genome, to allow for packaging of larger quantities of foreign DNA. See, e.g., Haj-ahmad and Graham (1986) *J. Virol.* 57:267–274 which describes adenovirus dlE1,3, an Ad5 virus which has most of the early region 3 (E3) and early region 1 (E1) deleted and therefore accepts up to about 7.5 kb of foreign DNA; Bett et al. (1993) *J. Virol.* 67:5911–5921, which discloses adenovirus mutants with 1.88 and 3.00 kb E3 deletions; Trapnell, B. C. (1993) *Advanced Drug Delivery Reviews* 12:185–199, describing Ad-dl327, an Ad5-derived mutant with a deletion of XbaI fragment D. Additionally, adenovirus chimeric vectors, such as those described in Michael et al. *J. Biol. Chem.* (1993) 268:6866–6869 and Wagner et al. *Proc. Natl. Acad. Sci. USA* (1992) 89:6099–6103, can also be used for gene delivery.

Other carrier viruses which will find use for the delivery of the various nucleic acid constructs to the target cell include those derived from the pox family of viruses, including vaccinia virus and avian poxvirus, as well as any of the various herpesviruses such as HSV, CMV, EBV, VZ etc. The use of these viruses to deliver gene sequences is well known in the art. Methods for the insertion of foreign genes in vaccinia virus have been described in detail. See, e.g., Mackett, M. et al. in *DNA Cloning: A Practical Approach*, vol. II (D. Glover, ed.) pp. 191–211; Mackett et al. (1984) *J. Virol.* 49:857–864; Fuerst et al. (1986) *Proc. Natl. Acad. Sci. USA* 83:8122–8126; and U.S. Pat. No. 4,722,848.

Alternatively, Avipoxviruses, such as the fowlpox and canarypox viruses, can also be used to deliver the constructs of the present invention. Methods for producing recombinant Avipoxviruses are known in the art and employ genetic recombination, as described above with respect to the production of vaccinia viruses. See, e.g., WO 91/12882; WO 89/03429; and WO 92/03545.

The nucleic acid constructs of the present nucleotide sequence integration system can be used to deliver selected sequences to a variety of cell and tissue types for the production of transgenic organisms, as well as for gene therapy, vaccination, or for characterizing a variety of genes and the mechanism of their actions. The instant methods will also find use in ribozyme and antisense therapy. For a review of antisense therapy and oligonucleotides useful in the same, see, Uhlmann, E. and Peyman, A. (1990) *Chem. Rev.* 90:543–584. For a discussion of ribozymes see, Cech et al. (1992) *J. Biol. Chem.* 267:17479–17482.

As presented above, site-specific integration of large pieces of DNA into the human genome is a desirable tool both for research purposes and for practical gene therapy applications. Site-directed recombination represents an efficient way of achieving site-specific integration. Currently, several site-directed recombination systems exist. For example, the yeast flip recombinase (FLP) can mediate recombination between two "flip recombination target sites" (FRT)—one present on a plasmid and one present in a specific location in the chromosomal DNA. O'Gorman et al., (1991) *Science* 251:1351–55. Similar results have been reported using the loxP-Cre recombination system. van Deursen et al (1995) *Proc. Natl. Acad. Sci. USA* 92:7376–80. Unfortunately, in both of these systems, the recombination site is not normally present in the human genome; instead, the site needs to be introduced, a very impractical process.

To overcome the problem of recombination systems presented in the preceding paragraph, a new system has been developed that is capable of mediating efficient site-specific integration of large pieces of DNA into a site normally present in all human cells. This adeno-associated virus-based system is termed "Targeted Vector Integration" (TVI). As previously alluded to, AAV requires the presence of a helper virus for efficient replication. In the absence of a helper virus coinfection, AAV integrates with high efficiency into human chromosome 19 (at position 19q13.3-qter).

As described above, AAV contains a large open reading frame, AAV rep, that encodes at least four proteins implicated in the replication of the virus. The four proteins—Rep 78, Rep 68, Rep 52 and Rep 40 —are named according to their apparent molecular weight. For a detailed description of the AAV genome, see, e.g., Muzyczka, N. (1992) *Current Topics in Microbiol. and Immunol.* 158:97–129; Kotin, R. M. (1994) *Human Gene Therapy* 5:793–801; Berns, K. I. "Parvoviridae and their Replication" in *Fundamental Virology*, 2nd Edition, (B. N. Fields and D. M. Knipe, eds.), pages 817–837. Rep 78 and Rep 68, termed the "long forms of Rep", are expressed from the p5 promotor (see below). The long forms of Rep possess a number of biochemical activities that directly implicates them in the replication of the virus. These activities include binding the viral inverted terminal repeats (ITRs), nicking at the terminal resolution site, and helicase activity. Kotin, R. M. (1994) *Human Gene Therapy* 5:793–801. In addition, it has been shown that Rep78 and Rep 68 mediate the formation of a complex between the ITR in the hairpin configuration and a 109 bp sequence from the AAV integration site that contains a similar 12 nucleotide core rep binding site. Kotin, R. M. (1994) *Human Gene Therapy* 5:793–801.

As previously alluded to, the present invention contemplates, among other things, the provision of a desired gene that encodes a protein that is defective or missing from a target cell genome in a patient. The present invention also contemplates a method of treating a patient suffering from a disease state by providing the patient with human cells genetically engineered to encode the required protein. In one embodiment, the cells may be genetically engineered in vitro by removing the cells from the patient, introducing the desired gene into the cells, then reintroducing the genetically engineered cells back into the patient. Of course, other methods of introducing desired genes into a patient are known and are within the scope of the present invention. For example, U.S. Pat. No. 5,399,346 to Anderson et al., which is hereby incorporated by reference, discusses several other methods that may be used in conjunction with the present invention.

C. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

In the disclosure which follows, the following abbreviations apply: ° C. (degrees Centigrade); $H_2O$ (water); HCl (hydrochloric acid); $MgSO_4$ (magnesium sulfate); $MgCl_2$ (magnesium chloride); aa (amino acid); PCR (polymerase chain reaction); kd or kD (kilodaltons); nt (nucleotides); gm (grams); $\mu$g (micrograms); mg (milligrams); ng (nanograms); $\mu$l (microliters); ml (milliliters); mm (millimeters); nm (nanometers); $\mu$m (micrometer); M (molar); mM (millimolar); MW (molecular weight); sec (seconds); min(s) (minute/minutes); hr(s) (hour/hours); ATCC (American Type Culture Collection, Rockville, Md.); DMEM (Dulbecco's Modification of Eagle's Medium); FBS (fetal bovine serum); dNTPs (deoxynucleotide triphosphates); BioRad (BioRad, Richmond, Calif.); Boehringer (Boehringer Mannheim Corp, Indianapolis, Ind.); Genome Systems (Genome Systems, Inc., St. Louis, Mo.); New England Biolabs (New England Biolabs, Inc., Beverly, Mass.); Novagen (Novagen, Inc., Madison, Wis.).

EXAMPLE 1

Direct Detection of Integration by PCR

In order to test whether Rep expression products facilitate integration of an AAV vector plasmid when transduced into a mammalian target cell, the following experiment was conducted.

A stable human cell line, 293, (readily available through, e.g., the American Type Culture Collection under accession number ATCC CRL1573) was grown to approximately 75% confluency in medium consisting of DMEM with 10% FBS and Pen/Strep. The 293 cells were then transfected with an AAV-LacZ vector plasmid (pAB11), using the calcium phosphate precipitation method. pAB11 was deposited with the American Type Culture Collection; pAB11 was assigned ATCC No. 98229 The AAV-LacZ vector, in a cassette cloned in the Pst1 site of pGEM-4 (Promega), included the AAV ITRs flanking a CMV promoter driving the LacZ gene.

The 293 cells were also transfected with AAV helper plasmids containing either the rep gene (pGN1980) or the rep and cap genes (pGN1764) or with the AAV-LacZ plasmid (pAB11) as a control. The rep containing plasmid included the AAV rep coding region (+145 to +2942, Srivastava et al. *J. Virol.* (1983) 45:555–564) cloned in the Sma1 site of pUC19 (New England Biolabs). The rep and cap containing plasmid included the same insert as pAAV-Ad (Samulski et al. *J. Virol.* (1989) 63:3822–3828) cloned in the Not1 site of pBSII KS- (Stratagene). Neither plasmid included the AAV ITRs. Shortly after the transfection, the 293 cells were infected with a freeze-thaw extract of adenovirus type 2. Three days later, total DNA was prepared from the cells.

Figure 2:
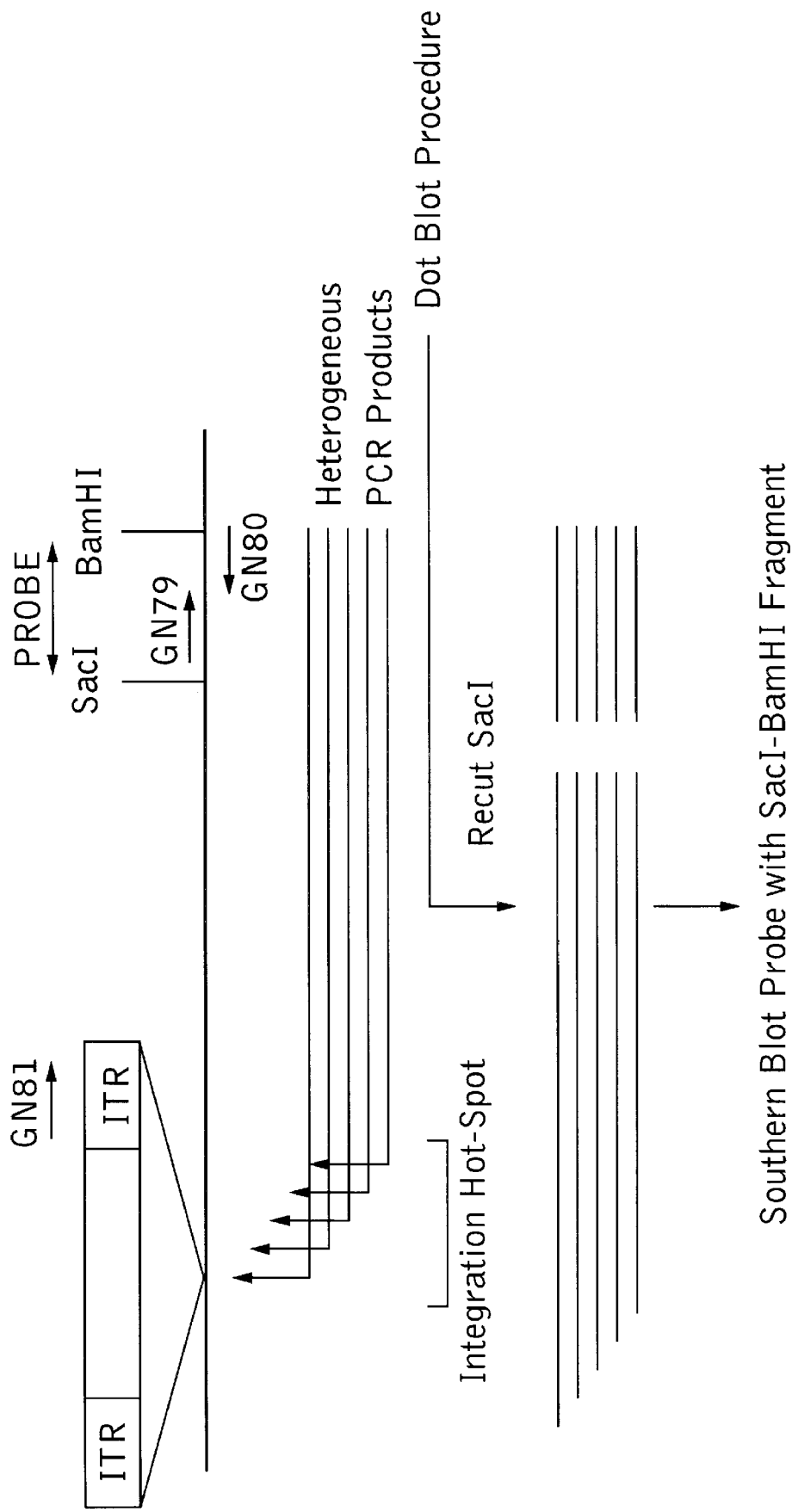
FIG. 2 diagrammatically depicts several strategies used in the examples to demonstrate rep mediated integration of the selected nucleotide sequence into chromosome 19 of the target cell.

If site-specific integration has occurred, it should be possible to detect it by PCR, using a pair of primers, one complementary to the AAV ITR and the other complementary to a region of chromosome 19 adjacent to the preferred AAV integration site. The PCR amplified DNA would be expected to be heterogeneous (FIG. 2) as template DNA is obtained from a pool of cells in which many integration reactions have occurred and as AAV integration sites in this region are spread over several hundred base pairs. However, after recutting the PCR amplified product with SacI, a 300 bp fragment should be generated. This fragment should hybridize to a Sac/Bam probe derived from the AAVS1 region. In other words, the presence of a 300 bp band on a Southern would be indicative of integration.

Thus, a PCR reaction was conducted as described above. For the PCR reaction, 200µM dNTPs were combined with 2µM of each primer, in 1×PCR buffer (Bochr Kit), 100 ng DNA and 1 unit of Taq polymerase. The amplification cycle proceeded for 15 seconds at 98° C.; 5 minutes at 94° C; 35 cycles for 1 minute at 94° C.; 1 minute at 55° C.; and 1 minute at 72° C.

The PCR product was recut with SacI by mixing 10 ml of amplified DNA with 2 units of SacI in 2 ml buffer A (10x) and 8 ml $H_2O$. The mixture was incubated at 37° C. for 1 hour to generate a 300 bp fragment which was amplified and resolved by electrophoresis and transferred to nitrocellulose. DNA from the cells cotransfected with both the AAV-LacZ and one or both of the helper plasmids hybridized to a 300 bp Sac/Bam probe derived from the AAVS1 region, indicating that site-specific integration had occurred.

EXAMPLE 2

Increased Frequency of Integration in the Presence of Rep Protein To test the hypothesis that Rep proteins increase the frequency of integration of an AAV plasmid vector into the chromosomal DNA of target mammalian cells, the following experiment was done. 293 cells were transfected either with an AAV-neo plasmid vector, pWP8-AAV-TK-neo, alone or cotransfected with pWP8 and either the rep containing plasmid (pGN1980) or rep and cap containing plasmid (pGN1764), both described above. To determine stable integration of the vector, the number of neo resistant colonies were counted for each vector construct as follows. Cells were placed under G418 selection (400 µg/mL) 48 hours after transfection. Media was replaced every 3 days. Plates were stained with a staining solution of 2% methylene blue 2% and 50% EtOH. After 2 minutes, the monolayers were washed and the stained clones counted.

The number of G418 recombinant colonies increased 3× in the presence of pGN1980 and 30×in the presence of pGN1764.

The above experiments indicates that efficient integration occurs in the target cell in the presence of Rep expression products. In both cases, the effect was more pronounced in the presence of pGN1764, suggesting that cap might stimulate this reaction. Alternatively, pGN1764 might simply express Rep better than pGN1980. Furthermore, the first experiment shows that at least some of the integration events are target specific as one of the two primers is homologous to AAVS1.

EXAMPLE 3

Identification of DNA Sequences Required For Integration

The previous examples have indicated that rep expression products facilitate integration of an AAV vector plasmid into a mammalian target cell. In order to identify the genetic elements in AAV vectors that contribute to integration, derivatives of pAAV carrying various mutations affecting the AAV coding region were tested.

Transfection experiments were conducted with the pAAV mutants. Three days after transfection, genomic DNA was prepared and submitted to a PCR dot blot procedure.

Cell Lines

Both the human embryonal kidney cell line, 293, and HeLa cells were used in the experiments of this example. The 293 cells are readily available through, e.g., the ATCC (ATCC accession number CRL1573). The HeLa cells are also readily available through the ATCC (e.g., number CCL2).

Plasmid Provirus And Mutants

Figure 3:
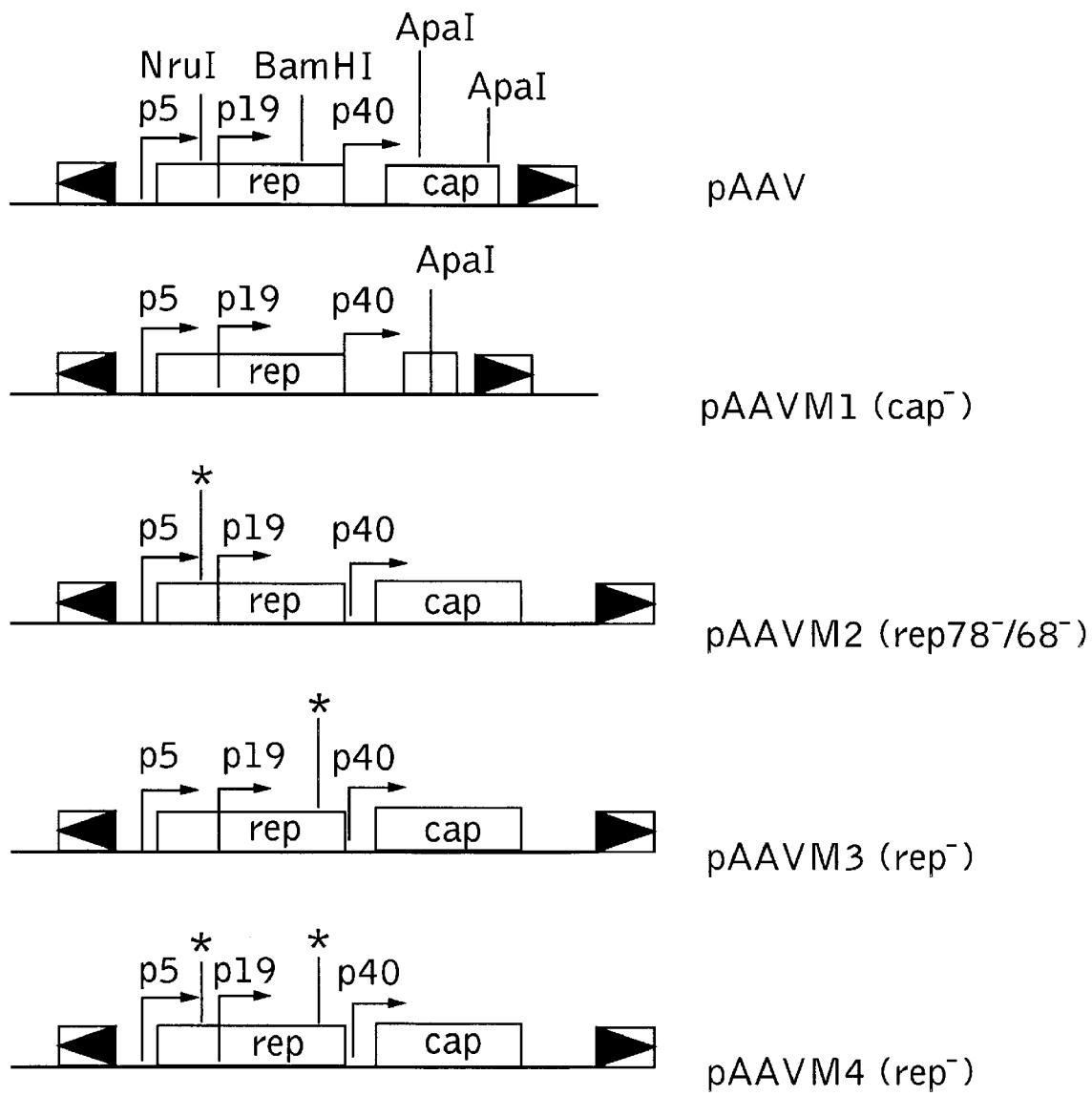
FIG. 3 depicts several diagrams of nucleic acid constructs of pAAV and derivatives thereof.

Referring to FIG. 3, pAAV is a plasmid carrying a replication-competent AAV provirus. pAAV is identical to psub201; the structure of psub201 is provided in U.S. Pat. No. 5,436,146 to Shenk et al. which is hereby incorporated by reference. Four mutants of pAAV were constructed: pAAVM1, pAAVM2, pAAVM3, and pAAVM4 (FIG. 3).

pAAVM1 contained a deletion in the cap region between ApaI sites at position 2943 and 4040. The other three derivatives (i.e., pAAVM2, pAAVM3, and pAAVM4) contained insertions in the rep region.

To construct pAAVM2, an 8 bp AscI linker (denoted by the ★) was inserted in the NruI site located on pAAV; this insertion results in a −1 frameshift affecting the p5-derived Rep 78 and Rep 68 proteins (the long forms of Rep). pAAVM3 was generated by treating BamHI-cut pAAV with Klenow enzyme (Boehringer) to fill in the ends; the blunt ends were then ligated together using standard ligation techniques, described above. The ★ represents the filled-in BamHI site. Because the BamHI site is situated downstream of both promoters, this mutation in pAAVM3 results in +1 frameshift affecting all four forms of Rep (ie., both the two short forms and the two long forms).

pAAVM4 is a double mutant carrying both frameshift mutations (ie., the frameshift mutations of pAAVM2 and pAAVM3). The two ★ symbols represent the position of the AscI linker and the filled-in BamHI site.

Transfection of 293 cells

The transfection procedure was performed according to the procedure that follows. The conditions were the same for both 293 cells and HeLa cells.

First, for each experimental condition, 2 ml cells were plated at a concentration of $4 \times 10^5$/mL in each well of a six-well plate. The culture media consisted of DMEM (Gibco #12-614F), 10% FBS (Hyclone # A-111-L), 50 units/mL Penicillin/50 units/ml streptomycin (Gibco #15070-014) and 2 mM L-glutamine (BioWhittaker #17-606E). The cells were incubated overnight at 37° C. in an atmosphere containing 5% $Co_2$.

Second, a calcium phosphate-DNA precipitate was prepared immediately before transfection. For each condition, 224 µL of Milli-Q (Class III) water were added. Next, 26 µL of 2.5M $CaCl_2$ were added, followed by 2 µg of each DNA. While bubbling the DNA mixture with a pasteur pipete, 250 µL of 2× HBS (274 mM NaCl, 10 mM KC1, 1.4 mM $Na_2HPO_4$, 12 mM dextrose, 42 mM Hepes, pH =7.05). This precipitate was added to each well (i.e., each experimental condition) dropwise.

Third, six hours later, the media and precipitate were aspirated from each well. Two mL of growth media were gently added, taking care not to disturb the cell monolayer. Next, the media was aspirated from the well, and 2 mL of fresh growth media were added. The plate was then returned to the incubator.

Extraction of Genomic DNA

After three days in culture, total genomic DNA was extracted from the pool of transfected cells. Genomic DNA was isolated for PCR and digestion by the same procedure, described below.

First, cells were trypsinized, then diluted in medium containing FBS to inactivate the trypsin and the cells were pelleted; the cell pellets were then resuspended in TE. Next, 0.5 mL of digestion DNA buffer (50 mM Tris, pH =8, 20 mM EDTA, 0.1 M NaCl, 1% SDS) and Proteinase K at a final concentration of 200 μg/mL (i.e., a 1:100 dilution of 20 mg/mL stock) were added. The digestion buffer was added at approximately 0.5 mL/1–5×10$^6$ cells or 0.5 mL/well of a six-well plate; for larger cell volumes, e.g., 10–20×10$^6$ cells, 2.5 mL per T75 flask or 10 cm dish can be added in a 15 mL tube. The cells were then incubated at 37° C. for approximately 1 hour.

Phenol/chloroform extraction was then performed (for larger preparations, the phases can be separated at 3000 rpm in 15 mL tubes in a Beckman GS-6R table top centrifuge). The upper aqueous phases were ethanol precipitated with 0.1 volumes of 3M sodium acetate and 3 volumes of ethanol at −80° C. for approximately 15 minutes. It was necessary to vigorously shake the preparations to ensure that the DNA was well mixed. The DNA was then formed into a pellet by microfuging at full speed for 15 minutes at 4° C. (for larger preparations, the DNA can be pelleted at 7000 rpm at 4° C.). Thereafter, the DNA was washed with 70% ethanol.

Finally, the DNA was resuspended in 100 μl of TE and RNase A at 10 μg/mL (for 1–5×10$^6$ cells in a six-well plate). For larger preparations, e.g., 10–20×10$^6$ cells (T75 flask or 10 cm dish), 500 μl of TE and RNaseA can be used. In addition, for larger preparations, DNA may require an overnight incubation at 37° C., with rotation, to enable the DNA to get into solution.

Description of Primers and Probes for PCR Dot Blot Procedure

Figure 4:
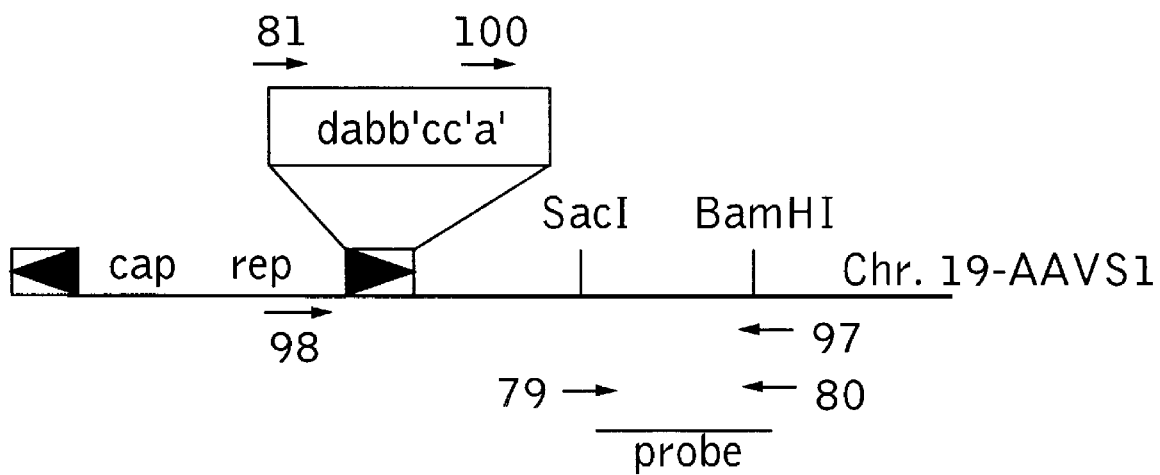
FIG. 4 is a diagram of the AAVS1 region of chromosome 19 depicting an AAV derivative (i.e., a provirus) integrated into the AAVS1 region. Each inverted viral terminal repeat is symbolized by an open rectangle containing a solid triangle; an expanded view of one of the ITRs is also shown. The numbered solid arrows represent primers.

FIG. 4 is a schematic map of the AAVS1 region of chromosome 19 depicting an AAV derivative (i.e., a provirus) integrated into the AAVS 1 region (the region is labeled as chr. 19-AAVS 1 in FIG. 4). As previously noted, the integration locus for AAV is human chromosome 19q13.3-qter; this is termed the "AAVS1 region". Samulski et al. (1991) *EMBO J.* 10:3941–3950; Kotin et al. (1992) *EMBO J.* 11:5071–5078. Referring to FIG. 4, the inverted viral terminal repeats are symbolized by open rectangles containing solid triangles; the points of the triangles indicate the direction or orientation of the ITR such that the triangles point away from the recombinant vector sequence. An expanded view of one of the ITRs is shown by the open rectangle containing the letters a, b, c, and d; each letter represents a discrete nucleic acid sequence. As discussed in further detail below, primer 100 is derived from the a',c' region of the AAV ITR and primer 81 is derived from the d region of the AAV ITR. The letters a', b', and c' represent the inverse sequence found in a, b, and c, respectively.

In FIG. 4, the location of primers complementary to sequences of the AAVS1 region or the integrated AAV derivative are indicated by arrows. The tip of the arrow represents the 3' end of the each primer. Primers 79, 80, and 97 are derived from AAVS1. The sequence of these primers are as follows: Primer 79: 5'-ACTTTGAGCTCTACTGGCTTC-3' (SEQ ID NO: 1); Primer 80: 5'-GGAGGATC CGCTCAGAGG-3' (SEQ ID NO:2); and Primer 97: 5'-CGGGGAGGATCCGCTCA GAGGTACA-3' (SEQ ID NO:3). As noted above, primers 81 and 100 are derived from (i.e., are complementary to) the AAV ITR. Kotin et al. (1992) *EMBO J* 11:5071–5078. The sequence of Primer 81 is 5'-AGGAACCCCT AGTGATGGAGT-3' (SEQ ID NO:4), and the sequence of Primer 100 is 5' -CGGCCTCAGTGAGCGAGCGCGC-3' (SEQ ID NO:5). Finally, Primer 98, derived from the p5 promotor, has the following sequence: 5'-CGCGTTCAAACCTCCCGCTTCAAAATG-3' (SEQ ID NO:6).

The location of a probe (double stranded DNA), a SacI/BamHI restriction fragment, complementary to the AAVS1 region is indicated by line labeled "probe" in FIG. 4.

PCR Dot Blot

The PCR Reaction

A PCR assay was used to detect site specific integration in unselected pools of transfected cells. If site specific integration has occurred, it should be possible to detect it by PCR, using a pair of primers, one complementary to the AAV ITR and the other complementary to the AAVS 1 region of chromosome 19 (i.e., 19q13.3-qter). The PCR amplified DNA would be expected to be heterogeneous (See FIG. 2), as template DNA is obtained from a pool of cells in which many integration reactions have occurred; moreover, wild type AAV is believed to integrate in a region of 19q13.3-qter spanning several hundred base pairs. However, all specific PCR amplification products, irrespective of their size, should hybridize to a SacI-BamHI fragment derived from the AAVS1 region. Thus, specific amplification products can be detected by DNA hybridization on dot blots using a SacI/BamHI probe derived from AAVS1 (FIG. 4).

The PCR reaction was performed according to the procedure described hereafter. An aliquot of DNA corresponding to 10$^4$ genomes (cells) was used in the PCR reaction. For the PCR reaction, 100μM dNTPs were combined with 1μM each of primers 97 and 100 in 1X NEB buffer for vent polymerase supplemented with 2 mM MgSO$_4$, and 2 units of Deep Vent$_R$® (exo) DNA polymerase (NEB). The cycle conditions were 10 seconds at 99° C. and 4 minutes at 72° C. for a total of 35 cycles.

For the Dot Blot procedure, 10% of the PCR reaction product was transferred to a nylon Zeta-Probe blotting membrane (Biorad) using a dot blot apparatus. That sample was then hybridized, according to the manufacturer's protocol, to the probe (i.e., the SacI/BamHI restriction fragment, derived from the AAVS1 region of chromosome 19). The probe comprised a random primed $^{32}$P labeled PCR fragment. The probe fragment was first generated by PCR, then labeled. The PCR comprised 0.1 μg of human genomic DNA and the primers were primer 79 and primer 80. The PCR conditions were as follows: 1× Taq buffer, 0.2 mM dNTP in a total volume of 90 μL. The PCR amplification was performed using Taq polymerase as follows: 1 cycle at 99° C. for 5 minutes, pause at 75° C., 97° C. for 5 seconds; 3 cylces at 97° C. for 10 seconds, 55° C. for 10 seconds, and 72° C. for 10 seconds; 32 cycles at 95° C. seconds, 55° C for 10 seconds, and 72° C. for 10 seconds. The labeling was conducted by random priming, as described above.

Validation of the PCR Assay

The PCR assay was validated using wild type AAV to infect the 293 cells and the HeLa cells. Initially, it should be noted that all of the results depicted in FIGS. 5A–B, 6, and 9 were obtained using the same pair of primers: primer 97 and primer 100. However, a signal (i.e., probe hybridization) was detected whether the virus-specific primer was homologous to the a,c region of the ITR (primer 100), the d region of the ITR (primer 81), or to the unique internal region of the virus (primer 98). The primers specific for the AAVS1 region of chromosome 19 (the region is labeled as chr.19-AAVS1 in FIG. 4) were also used successfully; these were primers 79, 80 and 97.

Figure 5A:
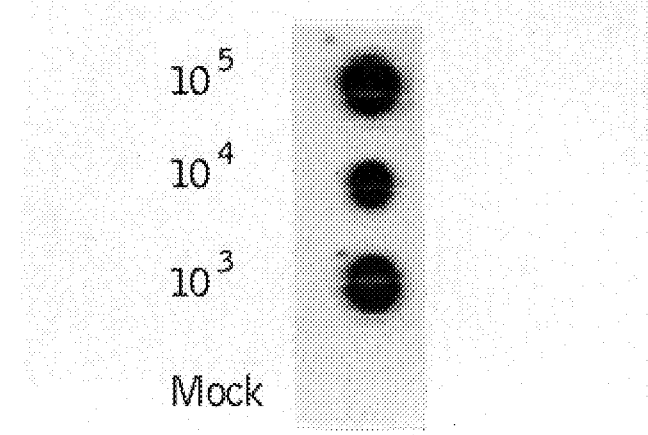
FIG. 5A indicates whether site specific integration occurred in 293 cells infected with wild type AAV2 at three different multiplicities of infection.
Figure 5B:
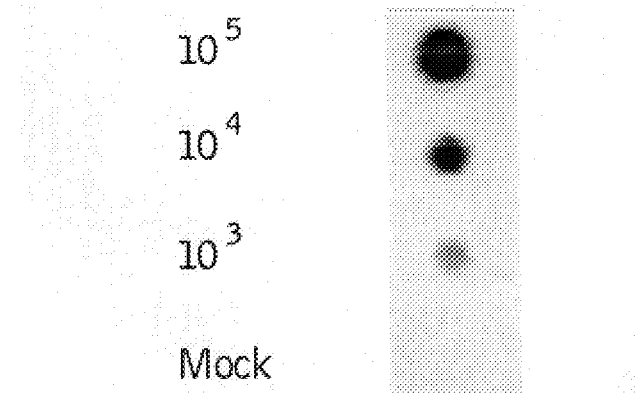
FIG. 5B indicates whether site specific integration occurred in HeLa cells infected with wild type AAV2 at three different multiplicities of infection.

FIG. 5A depicts the results of 293 cells infected with wild type AAV2 at three different multiplicities of infection (MOIs); FIG. 5B depicts the results obtained from analysis of HeLa cells infected with wild type AAV2 at three different MOIs $-10^3$, $10^4$, and $10^5$. As used herein, MOI is the number of single stranded genomes that infect each cell. Unless otherwise indicated, the results presented in FIGS. 5A and B were obtained using the same procedures. Referring to FIGS. 5A and B, a signal indicative of site specific integration was detected in both 293 cells and HeLa cells at all three MOIs tested; however, no signal was detected in the mock-infected cells.

The Results of the Transfection Experiments

Figure 6:
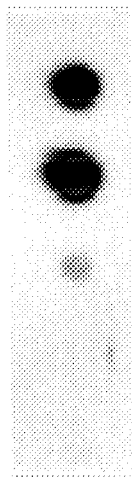
FIG. 6 indicates whether site specific integration occurred in 293 cells transfected with a recombinant AAV vector plasmid or derivatives thereof.

The results of the transfection experiments are depicted in FIG. 6. As one would expect, the cells transfected with pAAV indicate that integration has occurred. The pAAVMI proviral construct, containing an approximately 1 kb deletion in the cap gene, was able to integrate site specifically into AAVS1. In contrast, all frameshift mutations affecting the rep gene displayed significantly decreased levels of site specific integration.

These results demonstrated that the rep gene plays a critical role in targeting a mutant provirus to the AAVS1 region of chromosome 19 (i.e., 19q13.3-qter).

EXAMPLE 4

Rep Expression in trans Mediates Site-Specific Integration Of Large Pieces of DNA The experiments in Example 3 identified those DNA sequences required for integration. The experiments in this example are directed at indicating that rep expression in trans mediates site specific integration of large pieces of DNA.

Preparation of the Constructs

The Targeting Vectors

Figure 7A:
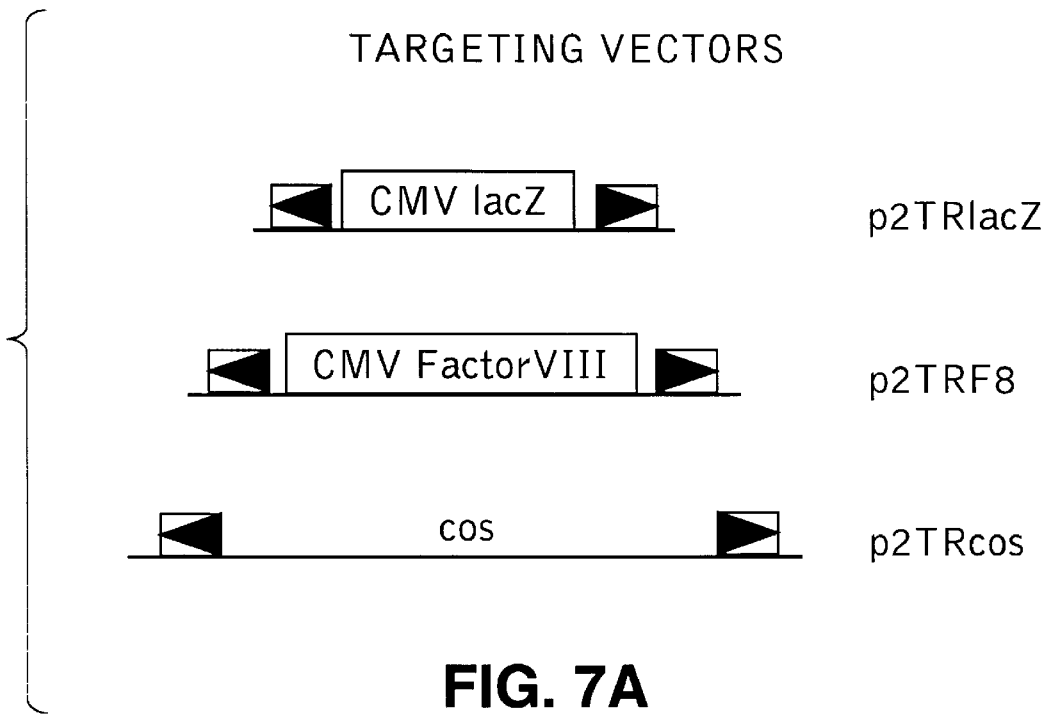
FIG. 7A depicts diagrams of targeting vectors used in the experiments described in the examples.

FIG. 7A depicts diagrams of the targeting vectors used in this example. In two of the targeting vectors (p2TRlacZ and p2TRF8), the rep and cap genes of pAVV (FIG. 3) were removed and replaced by (i) an expression cassette comprising the CMV promoter fused to the lacZ gene (p2TRlacZ), and (ii) an expression cassette comprising the CMV promoter fused to the human factor VIII cDNA (p2TRF8), respectively. For the third targeting vector (p2TRcos), an ITR -kan$^r$-ITR cassette was inserted into a yeast cosmid. Details regarding the construction of these vectors are presented below.

p2TRlacZ is a derivative of psub201 (see U.S. Pat. No. 5,436,146 to Shenk et al.) in which the XbaI fragment carrying the rep and cap genes present in psub201 were replaced with an expression cassette composed of the CMV promotor fused to the lacZ gene. p2TRlacZ was constructed according to the following procedure. First, an oligonucleotide encoding the restriction enzyme sites NotI-MluI-SnaBI-AgeI-BstBI-BssHII-NcoI-HpaI-BspEI-PmlI-RsrII-NotI (5'-GCGGCCGCACGCGTACGTACCGGTT CGAAGCGCGCACGGCCGACCATGGT- TAACTCCGGACACGTGCGGACCGCGGC CGC-3') (SEQ ID NO:7) was synthesized and cloned into pUC19 cut with KasI-EarI(partial) and blunted, producing a 2757 bp vector fragment. Second, three fragments were cloned into various sites of that 2757 bp vector fragment: (i) a 653 bp SpeI-SacII fragment encoding the CMV IE promoter was cloned into the SnaBI site; (ii) a 269 bp PCR-produced BstBI-BstBI fragment encoding the first intron of the hGH gene (the primers used were as follows: 5'-AAAATTCGAACAGGTAAGCGCCCCTTTG-3' (SEQ ID NO:8) and (5' -AAAATTCGAACCTGGGGAGAAACCAGAG-3' (SEQ ID NO:9)) was cloned into the BstBI site; and (iii) a 135 bp HpaI-BamHI(blunted) fragment containing the SV40 early polyadenylation site from pCMV-β was cloned into the HpaI site. Third, the resulting plasmid was cut with NotI and the CMVlacZ expression cassette was cloned into the psub201 vector fragment (containing the bacterial ori and amp$^r$ genes) which had been cut with XbaI, blunted, and linked with NotI linkers; this procedure resulted in the plasmid psub201CMV. Fourth, psub201CMV was then cut with BssHII(partial); a 3246 bp adhlacZ gene contained on a SmaI-DraI fragment derived from the plasmid pCMV-β (Clonetech) and linked with AscI linkers (5'-GAAGGC GCGCCTTC-3') (SEQ ID NO:10), was ligated to the BssHII-cut psub201CMV to create p2TRlacZ. It should be noted that because all of the linkers were obtained as single stranded DNA (in lysopholized form), the sequence identification numbers (SEQ ID NOs) list the linkers as being single stranded DNA.

p2TRF8 is identical to p2TRlacZ with the exception that the lacZ gene has been replaced with human factor VIII cDNA. p2TRF8 was constructed by replacing the adhlacZ gene in p2TRlacZ with human factor VIII eDNA (8968 bp) through the use of AscI linkers (using the same procedure as described above. The total size of this plasmid is approximately 14 kb, and the distance between the two ITRs is approximately 9.5 kb. p2TRF8 was deposited with the American Type Culture Collection; p2TRF8 was assigned ATCC No. 98230.

p2TRcos is a derivative of cPM9214, a cosmid obtained from the ATCC (# 70892) that consists of 28,010 base pairs of yeast DNA from the left arm of chromosome III cloned into the BamHI site of pHC79. Cosmid cPM9214 contains a unique Ecl136 II site. This unique Ecl136 II site was cut, and NotI linkers (5'-TTGCGGCCGCAA-3') (SEQ ID NO:11) were ligated to the ends, thereby creating a new cosmid (pRR23) containing a unique NotI site. Thereafter, pRR23 was cut with NotI, and a NotI restriction fragment carrying an ITR-kan$^r$-ITR cassette (described below) was inserted in the NotI site, thereby creating cosmid p2TRcos.

Figure 8:
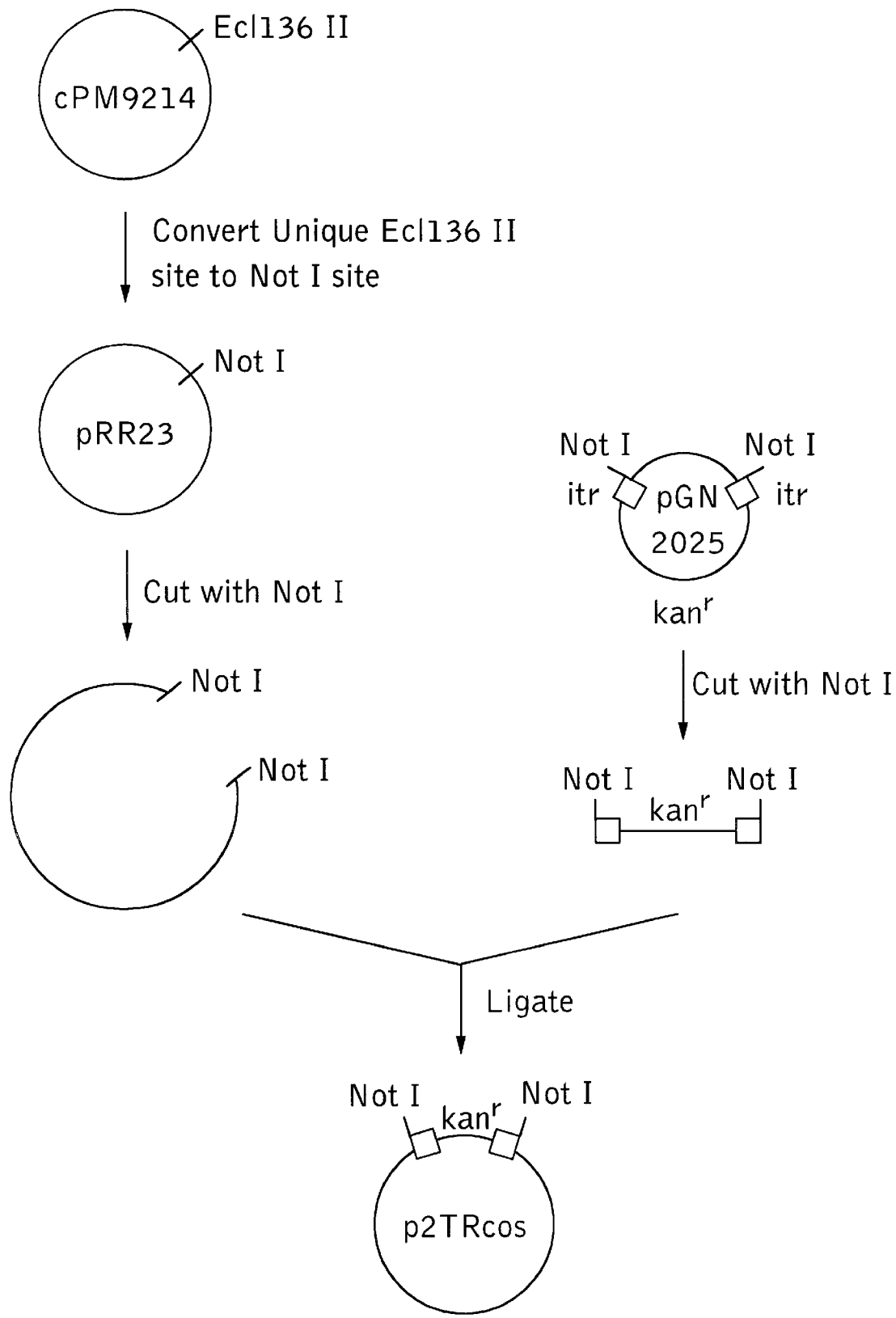
FIG. 8 is a diagram illustrating steps used in the construction of p2TRcos.

The ITR-kan$^r$-ITR cassette inserted into the NotI site was constructed as follows. The ITRs from psub201 were modified to add Sse I and NotI linkers in order to achieve the following structures: 5'ITR: SseI-PvuII-ITR-XbaI-NotI; 3' ITR: NotI-XbaI-ITR-PvuII-SseI. Next, a 1772 bp fragment containing the kan' gene was obtained from plasmid pBK/ CMV (Stratagene) by digestion with BspHI; this fragment was then treated with Klenow enzyme in the presence of dNTPs and SseI linkers were ligated to each end. After digestion with SseI, the fragment was ligated to the AAV ITRs described above to obtain the fragment 5'-NotI-XbaI-ITR-PvuII-SseI-kan$^r$-SseI-PvuII-ITR-XbaI-NotI-3' (i.e., the ITR-kan$^r$-ITR cassette). This cassette was then inserted into the NotI site of pRR23, as described above. FIG. 8 diagramatically depicts the methods used in the construction of p2TRcos. It should be noted that the orientation of the ITRs relative to the kan gene is opposite the orientation of the ITRs to the rep and cap genes in an AAV provirus.

The Helper Plasmids

Figure 7B:
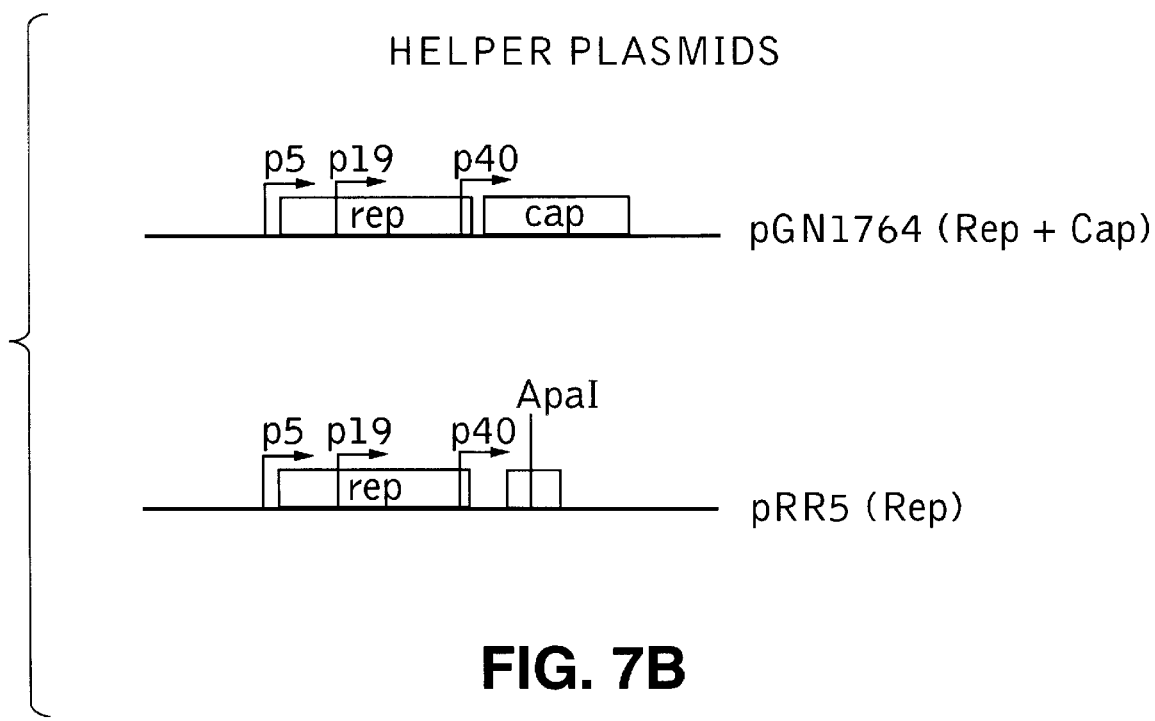
FIG. 7B depicts diagrams of helper plasmids used in the experiments described in the examples.

FIG. 7B depicts diagrams of the helper vectors used in this example. In FIG. 7B, the following abbreviations and symbols are used: the open rectangle labeled "rep" in its interior (coding region, i.e., open reading frame, for the rep gene); the open rectangle labeled "cap" in its interior (coding region, i.e., open reading frame, for the cap gene); the solid triangles with a vertical line attached (location of the endogenous promoters for encoding p5, p19, and p40 proteins). See, e.g., Muzyczka, N. (1992) *Current Topics in Microbiol. and Immunol.* 158:97–129; Bems, K. (1990) *Microbiol. Rev.* 54(3):316–29.

Two AAV helper plasmids were constructed: (i) pGN1764, which includes the AAV rep and cap coding regions (described in Example 1, and (ii) pRR5 , which includes the AAV rep coding region and only part of the cap coding region.

pGN1764 contains the entire AAV coding region. This plasmid included the same insert as that found on pAAV-Ad (Samulski et al. *J. Virol.* (1989) 63:3822–3828) isolated as a NotI restriction fragment cloned in the NotI site of pBSII KS- (Stratagene). All three endogenous promoters (p5, p19 and p40, indicated by arrows in FIG. 7B) are present in this construct.

pRR5 was constructed as follows. First, psub201 was digested with ApaI, the 1103 base pair fragment in the cap region was removed, and then the two ends were religated. The resulting construct was then digested with XbaI, to create a 3.2 kb AAV genomic fragment. That 3.2 kb fragment was subsequently inserted into the SpeI site of p680E3Δ (Ketner et al., (1994) PNAS 91(13):6186–90) to produce pRR5. Again, all three endogenous promoters (p5, p19 and p40, indicated by arrows in FIG. 7B) are present in this construct; the ApaI restriction site is also depicted in FIG. 7B.

Transfection of 293 Cells

Figure 9:
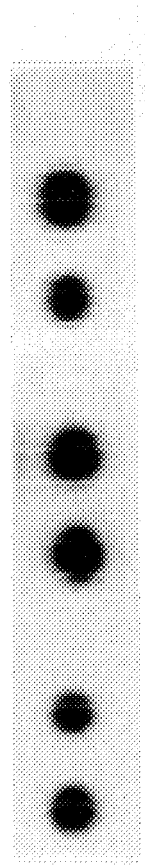
FIG. 9 indicates whether site specific integration occurred in 293 cells transfected alone with either p2TRlacZ, p2TRF8, or p2TRcos; cotransfected with either p2TRlacZ and pRR5, p2TRF8 and pRR5, or p2TRcos and pRR5; and cotransfected with either p2TRlacZ and pGN1764, p2TRF8 and pGN1764, or p2TRcos and pGN1764.

Human embryonal kidney cell line 293 was used in this experiment. This experiment tested whether cotransfection of a targeting vector with a Rep-expressing plasmid was sufficient to cause site specific integration of the targeting vector, containing large nucleotide sequences, whose only AAV-derived sequences are the two ITRs. In this experiment, three ITR-containing vectors (described above) were used: (i) p2TRlacZ, an expression cassette comprising the CMV promoter fused to the lacZ gene, (ii) p2TRF8, an expression cassette comprising the CMV promoter fused to the human factor VIII cDNA; and (iii) p2TRcos, a cosmid containing a ITR -kan$^r$-ITR cassette in which the orientation of the ITRs relative to the kan gene is opposite the orientation of the ITRs to the rep and cap genes in an AAV provirus. These plasmids were transfected either alone or along with either one of two Rep-expressing plasmids (pGN1764 and pRR5). The results of this experiment are depicted in FIG. 9 and described below.

Cell Cultures and Extraction of Genomic DNA

The protocols for culturing the 293 cells and for extracting the genomic DNA were identical to the protocols set forth in Example 3. After three days in culture, total genomic DNA was extracted from the transfected cells. An aliquot of DNA corresponding to $10^4$ genomes was used in a PCR Dot Blot procedure. The PCR reaction and Dot Blot procedure was also performed identically to the description provided in Example 3.

Site Specific Targeting

As depicted in FIG. 9, site specific integration did not occur when the three ITR-containing plasmids (i.e., p2TRlacZ, p2TRF8, and p2TRcos) were transfected into 293 cells alone; the lack of site specific integration is indicated by the absence of a strong signal. However, cotransfection with both Rep-expressing plasmids (i.e., pGN1764 and pRR5) resulted in the integration of all three ITR-containing plasmids.

The results indicate that rep expression in trans mediates site-specific integration. Moreover, the integration of p2TRF8 and pTRcos indicates that it is possible to target large pieces of DNA that play an important role in disease states and the like. Indeed, it might be possible to integrate DNA sequences of approximately 100 kb or more.

EXAMPLE 5

Confirmation of Chromosomal Location

The experiments described in this example are directed at confirming the chromosomal location of the integrated target vectors. More specifically, the experiments in this example indicate that site specific integration occurs into the AAVS1 region of chromosome 19.

Preparation of Nucleic Acid Constructs

The following constructs were used in this example: the target vector p2TRlacZ and the helper plasmids pRR5 and pRSVRepCap. The p2TRlacZ and pRR5 were constructed as described in Example 4. pRSVRepCap was constructed as described below.

pRSVRepCap was constructed according to the following procedure. First, a Bg III linker was inserted into the AAV genome (pGN1764) at the HhaI site eleven nucleotides 5' to the ATG codon of Rep 78; this insertion resulted in the creation of pGN1782. pGN1782 was then digested with BglII and XbaI to yield a 4174 bp fragment containing the rep and cap coding sequences, but lacking the p5 promoter. This fragment was then treated with Klenow enzyme in the presence of dNTPs and ligated with NotI linkers. Thereafter, the fragment was digested, with NotI, gel purified, and ligated into the NotI site of pORSVICAT (Stratagene). The resulting plasmid, pROS-001, contained the RSV promoter immediately 5' of the ATG of Rep 78.

pRSVRepCap was constructed from pROS-001. First, pROS-001, which contains a unique SnaBI site, was digested with SnaBI. Then, an XbaI-HinDIII fragment was derived from the simian virus 40 (SV40) origin of replication by digesting with XbaI and HinDIII. This XbaI-HinDIII fragment was then treated with Klenow enzyme in the presence of dNTPs and inserted into the unique SnaBI site of pROS-001, resulting in pRSVRepCap.

β-galactosidase Protocol

The production of β-galactosidase by cells allowed detection of those cells successfully transfected in order to pick clones of cells that could then be expanded. The following reagents, supplies, and methods were used in the β-galactosidase procedure described below.

tissue culture reagents and supplies (i) DMEM (Bio-Whittaker cat. # 12-614F), containing 10% fetal calf serum (HyClone cat #A1111-L, heat-inactivated at 56° C. for 1 hour), 50 units/mL of penicillin G, 50 units/mL of streptomycin (GibcoBRL cat. #15070-014) and 2 mM L-glutamine (Bio-Whittaker cat #17-650E); (ii) Dulbecco's phosphate-buffered saline without calcium and magnesium (Hyclone cat #B-4004-L); (iii) 0.25% trypsin solution with EDTA (Hyclone Cat #B-3004-D); (iv) 75 cm$^2$ tissue culture flasks (Corning cat. #430641); and (v) 12-well tissue culture plates (well diameter 2.2 cm; Coming cat #25815).

assay reagents: (i) fixative solution

The fixative solution consisted of Dulbecco's phosphate buffered saline without calcium and magnesium (HyClone catalog-B-4004-L) containing 2% formaldehyde and 0.2% glutaraldehyde. The solution was prepared by combining Dulbecco's PBS, 25% aqueous glutaraldehyde, and 37% formaldehyde. The fixative solution was prepared fresh on the day it was used. (ii) staining buffer: The staining buffer consisted of Dulbecco's phosphate buffered saline without calcium and magnesium (HyClone cat.-B-4004-L) containing 5mM $K_3Fe(CN)_6$, 5mM $K_4Fe(CN)_6$, and 2mM $MgCl_2$. This solution was prepared from the following stock reagents: Dulbecco's PBS, 200 mM $K_3Fe(CN)_6$, 200 mM $K_4Fe(CN)_6$, and 1M $MgCl_2$ (store the 200 mM $K_3Fe(CN)_6$ and $K_4Fe(CN)_6$ solutions in the dark at 4° C.). The staining buffer solution was prepared fresh on the day it was to be used. (iii) X- gal stock solution: The X-gal solution (5-bromo-4-chloroindolyl- β-galactaside) consisted of 40 mg/ml X-gal in dimethylformamide. The solution was stored at −20° C. in the dark. (iv) substrate solution: Staining buffer with a final concentration of I mg/ml X-gal. Prepare no more than 30 minutes before use.

fixation and staining of cells

The reagents were prepared in the following manner: (i) fixative solution: for 100 mLs, 0.8 of 25% aqueous glutaraldehyde and 5.4 mL of 37% formaldehyde were added to 93.8 mL of dulbecco's PBS. The fixative solution and an equal volume of Dulbecco's PBS (for rinse) were placed on ice; (ii) staining buffer: for 100 mLs, add 2.5 mL of 200 mM $K_3Fe(CN)_6$, 2.5 mL of 200 mM $K_4Fe(CN)_6$, and 0.2 mL of 1 M $MgCl_2$ were added to 94.8 mL of Dulbecco's PBS; and (iii) substrate solution: this solution should be prepared no more than 30 minutes before use. For 100 mLs, 97.5 mL of staining buffer were warmed to 37° C., 2.5 mL of X-gal stock solution (40 mg/mL X-gal in dimethylformamide) were added, and the resulting solution was mixed well. This solution was kept at 37° C. until used.

Each well of the 12-well tissue culture plate to be stained required 1 mL of fixative solution, 1 mL of Dulbecco's PBS, and 1 mL of substrate solution. First, the medium was aspirated from the wells, 1 mL of cold fixative solution was added, and then a 5 minute incubation period was commenced. Second, the fixative solution was aspirated, the wells were washed once with 1 mL of Dulbecco's PBS, and then replaced with 1 mL of warm substrate solution. Finally, the plate was incubated for 24 hours at 37° C. (do not use a $CO_2$ incubator) in the dark (wrapped in aluminum foil). Although the cell cultures began to stain immediately, they required 24 hours to fully develop before counting.

Transfection of 293 Cells

Human embryonal kidney cell line 293 were used in this experiment. Pools of cells were cotransfected with either p2TRlacZ and pRR5 or with p2TRlacZ and pRSVRepCap. Referring to the results of the Southern Blot depicted in FIG. 10, lane 4 represents cells cotransfected with p2TRlacZ and pRR5, lanes 1–3 and 5–7 represent cells cotransfected with p2TRlacZ and pRSVRepCap, and lane 8 is the control (293 cells).

During the post-transfection period between day 2 and day 28, single cell clones were isolated from pooled populations by FAC sort or limiting dilution. These single-cell clones were then expanded, and the clones were screened for β-galactosidase production. Production of β-galactosidase, resulting from the expression of the lacZ gene, was determined using the materials and methods described above. Seven clones positive for β-galactosidase were chosen at random and expanded.

Preparation of Genomic DNA Extracts

Genomic DNA (10 μg from each clone) from the seven β-galactosidase positive clones was restricted with HinDII-Isite estriction enzyme that has no restriction site in either the AAVS1 region or in p2TRlacZ. The resulting digests were then resolved by electrophoresis on a 0.8% agarose gel (Gibco-BRL), and the product was transferred to a nitrocellulose membrane (Schlechter and Schuell).

Southern Blot Analysis

Figure 10:
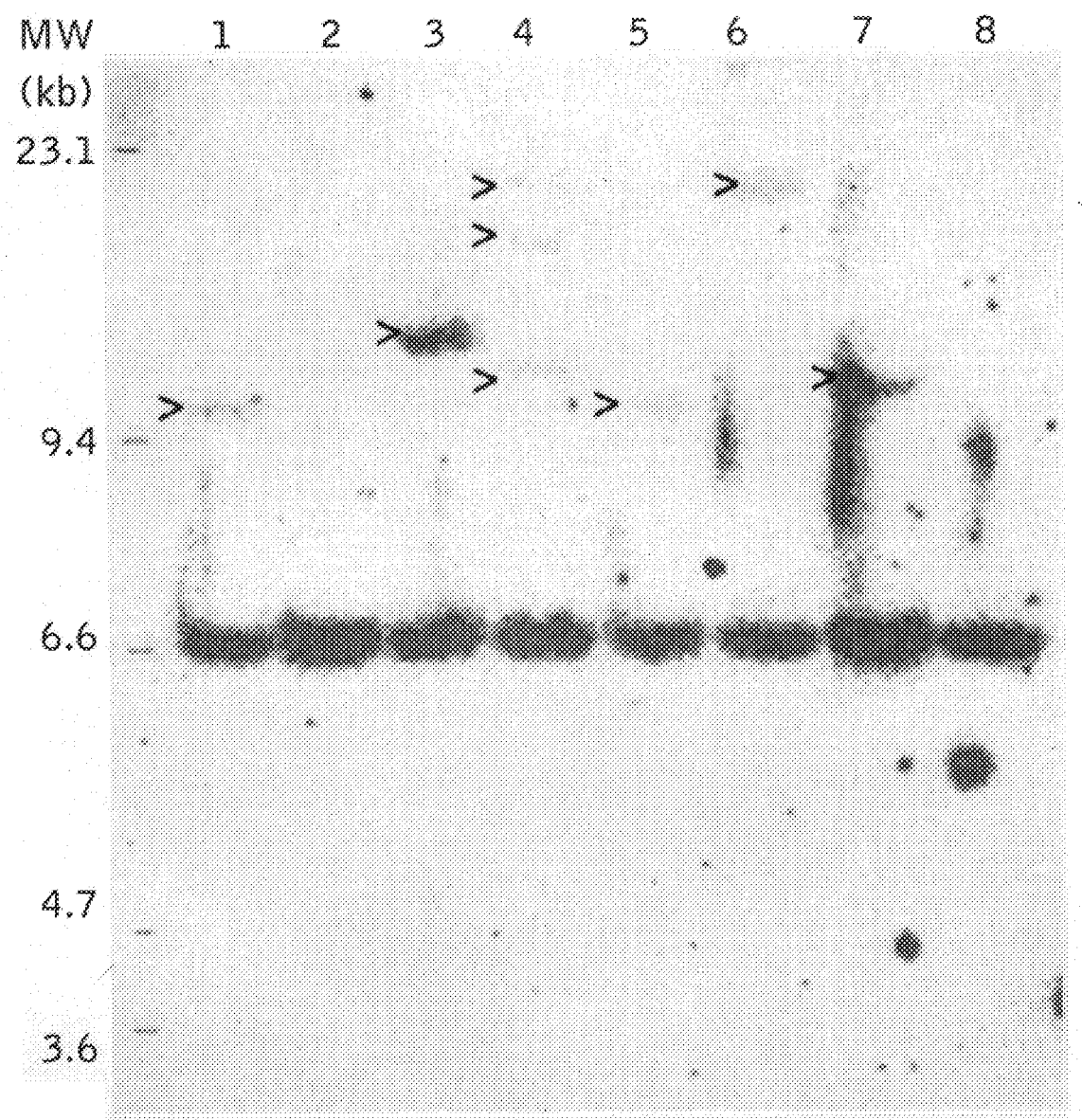
FIG. 10 depicts the results of a Southern Blot performed on β-galactosidase-positive clones of 293 cells transfected with a targeting vector and a helper plasmid.

The genomic DNA extracts were then analyzed by Southern blot using an AAVS1 probe (a 3.5 kb EcoRI-KpnI fragment derived from the AAVS1 region of chromosome 19). FIG. 10, a Southern blot, depicts the results of the hybridization analyses; each of lanes 1–7 contained the genomic DNA extract from one of the β-galacatasidase-positive clones. An understanding of the significance of restricting the DNA with HinDIII is helpful when reviewing the results in FIG. 10. While the exact location of the HinDIII sites are unknown, it is known that a HinDIII restriction site lies on either side of the AAVS1 region; however, there is no HinDIII site within that region. Thus, hybridization of non-transfected 293 cells with the probe yielded, as expected, a single band (FIG. 10, lane 8, 6.6 kb).

Conversely, the site specific integration of DNA sequences by transfection introduces additional HinDIII sites in the AAVS1 region. Therefore, more than one restriction fragment from the AAVS1 region should be formed upon digestion with HinDIII, and more than one band should be visible when probed with the AAVS 1 fragment. Reference to FIG. 10 reveals that a genomic event (indicated by the >symbol) appeared in lanes 1 and 3–7. That is, site specific integration occurred in the clones in each of those lanes. The rearrangements of the AAVS1 region are different in each clone, as indicated by the different positions of the additional hybridization bands in each of those lanes. In one case (lane 4), three AAVS1 hybridizing bands are visible in addition to the single band present in the parent 293 cells. The genomic DNA from that clone was subsequently used in the fluorescent in situ hybridization, described below.

Fluorescent in situ Hybridization

Fluorescent in situ hybridization was performed in order to definitively show that p2TRlacZ was linked to the AAVS1 region. The β-galactosidase-positive clone (cotransfected with pRR5) that yielded three hybridizing bands in the Southern blot was used in this analysis (FIG. 10, lane 4).

Metaphase chromosomes were prepared by usual cytogenetic means from cell line 293 lac z (CRL1573). Purified DNA from plasmid clone p2TRlacZ was labeled with digoxigenin dUTP by nick translation. Labeled probe (p2TRlacZ) was combined with sheared human DNA and cohybridized to metaphase chromosomes with a probe (Genome Systems) from the E2A locus (in a solution containing 50% formamide, 10% dextran sulfate, and 2X SSC). Specific hybridization signals were detected and amplified by the sequential application of fluroesceinated sheep antidigoxigenin antibodies and fluoresceinated rabbit antisheep antibodies; this was followed by counterstaining with propidium iodide.

Figure 11:
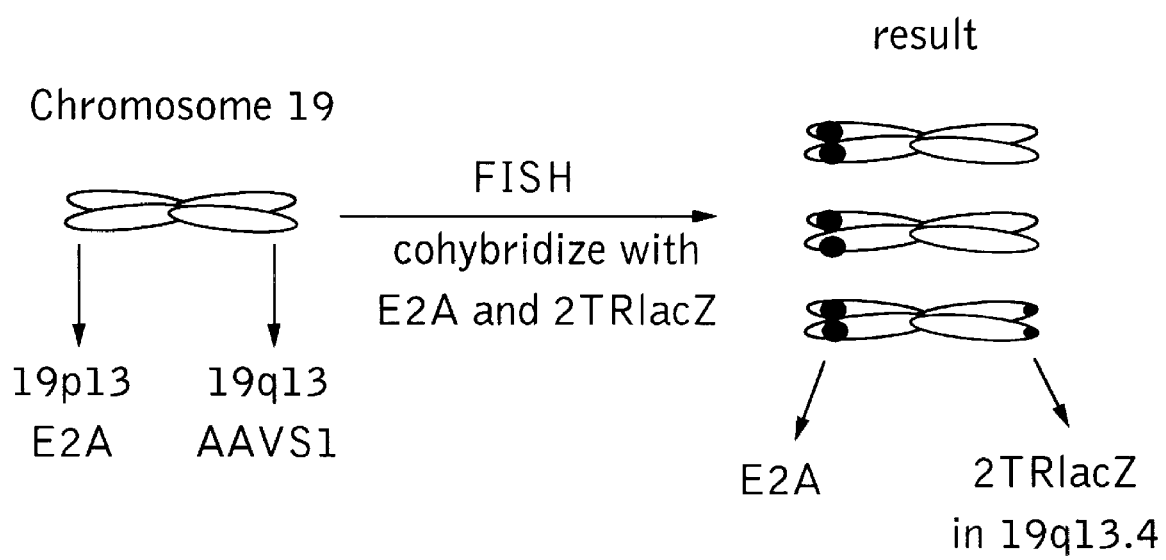
FIG. 11 diagramatically illustrates the fluorescence in situ hybridization (FISH) strategy used in the examples.

The method is diagrammatically depicted in FIG. 11. Referring to FIG. 11, the p2TRlacZ probe was used to mark the integration site of p2TRlacZ in the AAVS1 region of chromosome 19; the E2A probe was used to mark the p arm of all of the copies of chromosome 19 present in the cell (i.e., the E2A probe specifically identifies the p arm on chromosome 19). This experiment resulted in the labelling, by the E2A probe, of at least three copies per cell of chromosome 19 at 19p13 and the labelling, by the 2TRlacZ probe, of 1 copy of chromosome 19 at 19q13.4.

These results indicate that p2TRlacZ is integrated into a single homologue of chromosome 19 at a position near the q terminus. All copies of chromosome arm 19p were marked with the hybridization signals from the E2A probe, which demonstrated that the p2TRlacZ integration site is on the q arm of chromosome 19.

Thus, novel AAV derived vector systems for gene delivery and integration are disclosed. Although preferred embodiments of the subject invention have been described in some detail, it is understood that obvious variations can be made without departing from the spirit and the scope of the invention as defined by the appended claims.

What is claimed is:

1. A method of integrating a selected nucleotide sequence into the genome of a mammalian cell, comprising:
   (a) providing:
      (i) a mammalian cell;
      (ii) a first virion-free nucleic acid construct comprising a nucleotide sequence flanked by a 5' and a 3' adeno-associated virus inverted terminal repeat; and
      (iii) a second virion-free nucleic acid construct having a rep coding region operably linked to control elements which direct the transcription and translation of the rep coding region in said mammalian cell;
   (b) introducing, in any order, said first and second virion-free nucleic acid constructs into said mammalian cell; and
   (c) expressing the rep coding region of said second nucleic acid construct, thereby producing an amount of rep expression product under conditions such that an increased frequency of integration of said nucleotide sequence of said first nucleic acid construct into the genome of said mammalian cell is achieved.

2. The method of claim 1, wherein said inverted terminal repeats in said first nucleic acid construct were excised from said adeno-associated virus.

3. The method of claim 1, wherein said first nucleic acid construct and said second nucleic acid construct are present on the same vector.

4. The method of claim 1, wherein said first nucleic acid construct and said second nucleic acid construct are present on different vectors.

5. The method of claim 1, wherein said nucleotide sequence of said first nucleic acid construct is integrated into chromosome 19 q of said mammalian cell.

6. The method of claim 1, wherein said nucleotide sequence of said first nucleic acid construct is more than 5,000 base pairs.

7. The method of claim 1, wherein said nucleotide sequence of said first nucleic acid construct encodes a polypeptide.

8. The method of claim 2, wherein said first nucleic acid construct is contained in a plasmid.

9. The method of claim 8, wherein said mammalian cell is transfected with said plasmid.

10. The method of claim 6, wherein said nucleotide sequence of said first nucleic acid construct is more than 10,000 base pairs.

11. The method of claim 7, wherein said polypeptide encodes at least a portion of the factor VIII gene.

12. A method of integrating a selected nucleotide sequence into the genome of a mammalian cell, comprising:
   (a) providing:
      (i) a mammalian cell;
      (ii) a first virion-free nucleic acid construct comprising a nucleotide sequence flanked by a 5' and a 3' adeno-associated virus inverted terminal repeat, and
      (iii) an amount of rep expression product which increases the frequency of integration of said nucleotide sequence of said first nucleic acid construct;
   (b) introducing said first nucleic acid construct and said rep expression product, in any order, into said mammalian cell; and
   (c) integrating said nucleotide sequence of said first nucleic acid construct into said mammalian cell, under conditions such that an increased frequency of integration of said nucleotide sequence of said first virion-free nucleic acid construct is achieved by said rep expression product.

13. The method of claim 12, wherein said inverted terminal repeats in said first nucleic acid construct were excised from said adeno-associated virus.

14. The method of claim 12, wherein the mammalian cell is transfected with said plasmid.

15. The method of claim 12, wherein said nucleotide sequence of said first nucleic acid construct is integrated into chromosome 19 q of said mammalian cell.

16. The method of claim 12, wherein said nucleotide sequence of said first nucleic acid construct is more than 5,000 base pairs.

17. The method of claim 12, wherein said nucleotide sequence encodes a polypeptide.

18. The method of claim 13, wherein said first nucleic acid construct is contained in a plasmid.

19. The method of claim 16, wherein said nucleotide sequence of said first nucleic acid construct is more than 10,000 base pairs.

20. A mammalian cell, comprising:
   (a) a virion-free first nucleic acid construct comprising a nucleotide sequence flanked by a 5' and a 3' adeno-associated virus inverted terminal repeat; and
   (b) a virion-free second nucleic acid construct having a rep coding region operably linked to control elements which direct the transcription and translation of the rep coding region in said mammalian cell to produce an amount of rep expression product to increase the frequency of integration of said nucleotide sequence of said first nucleic acid construct and said nucleotide sequence of said first nucleic acid construct is integrated into the genome of said mammalian cell.

21. The mammalian cell of claim 20, wherein said inverted terminal repeats in said first nucleic acid construct were excised from said adeno-associated virus.

22. The mammalian cell of claim 20, wherein said first nucleic acid construct and said second nucleic acid construct are present on the same vector.

23. The mammalian cell of claim 20, wherein said first nucleic acid construct and said second nucleic acid construct are present on different vectors.

24. The mammalian cell of claim 20, wherein said nucleotide sequence of said first nucleic acid construct is integrated into chromosome 19 q of said mammalian cell.

25. The mammalian cell of claim 20, wherein said nucleotide sequence of said first nucleic acid construct is more than 5,000 base pairs.

26. The mammalian cell of claim 20, wherein said nucleotide sequence of said first nucleic acid construct encodes a polypeptide.

27. The method of claim 20, wherein said polypeptide encodes at least a portion of the factor VIII gene.

28. The mammalian cell of claim 21, wherein said first nucleic acid construct is contained in a plasmid.

29. The mammalian cell of claim 28, wherein said plasmid is transfected into said mammalian cell.

30. The mammalian cell of claim 25, wherein said nucleotide sequence of said first nucleic acid construct is more than 10,000 base pairs.

31. The mammalian cell of claim 26, wherein said polypeptide encodes at least a portion of the factor VIII gene.

32. A mammalian cell, comprising:
   (a) a nucleic acid construct comprising a nucleotide sequence flanked by a 5' and a 3' adeno-associated virus inverted terminal repeat; and
   (b) an amount of rep expression product which increases the frequency of integration of said nucleotide sequence of said nucleic acid construct into the genome of said mammalian cell.

33. The mammalian cell of claim 32, wherein said inverted terminal repeats in said nucleic acid construct were excised from said adeno-associated virus.

34. The mammalian cell of claim 32, wherein said nucleic acid construct is contained in a plasmid.

35. The mammalian cell of claim 32, wherein said plasmid is transfected into said mammalian cell.

36. The mammalian cell of claim 32, wherein said nucleotide sequence of said nucleic acid construct is integrated into chromosome 19 q of said mammalian cell.

37. The mammalian cell of claim 32, wherein said nucleotide sequence of said nucleic acid construct is more than 5,000 base pairs.

38. The mammalian cell of claim 32, wherein said nucleotide sequence of said first nucleic acid construct encodes a polypeptide.

39. The mammalian cell of claim 37, wherein said nucleotide sequence of said nucleic acid construct is more than 10,000 base pairs.

40. The mammalian cell of claim 38, wherein said polypeptide encodes at least a portion of the factor VIII gene.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

ACTTTGAGCT CTACTGGCTT C            21

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

GGAGGATCCG CTCAGAGG            18

( 2 ) INFORMATION FOR SEQ ID NO:3:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

CGGGGAGGAT CCGCTCAGAG GTACA      25

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

AGGAACCCCT AGTGATGGAG T           21

( 2 ) INFORMATION FOR SEQ ID NO:5:

( i ) SEQUENCE CHARACTERISTICS:
        ( A ) LENGTH: 22 base pairs (B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:5:

CGGCCTCAGT GAGCGAGCGC GC 22

(2) INFORMATION FOR SEQ ID NO:6:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:6:

CGCGTTCAAA CCTCCCGCTT CAAAATG 27

(2) INFORMATION FOR SEQ ID NO:7:

(i) SEQUENCE CHARACTERISTICS:
(A) LENGTH: 80 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:7:

GCGGCCGCAC GCGTACGTAC CGGTTCGAAG CGCGCACGGC CGACCATGGT TAACTCCGGA 60

CACGTGCGGA CCGCGGCCGC 80

(2) INFORMATION FOR SEQ ID NO:8:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:8:

AAAATTCGAA CAGGTAAGCG CCCCTTTG 28

(2) INFORMATION FOR SEQ ID NO:9:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:9:

AAAATTCGAA CCTGGGGAGA AACCAGAG 28

(2) INFORMATION FOR SEQ ID NO:10:

(i) SEQUENCE CHARACTERISTICS:
(A) LENGTH: 14 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:10:

GAAGGCGCGC CTTC                                                                                                  14

(2) INFORMATION FOR SEQ ID NO:11:

(i) SEQUENCE CHARACTERISTICS:
      (A) LENGTH: 12 base pairs
      (B) TYPE: nucleic acid
      (C) STRANDEDNESS: single
      (D) TOPOLOGY: linear (i i) MOLECULE TYPE: DNA (genomic)

(x i) SEQUENCE DESCRIPTION: SEQ ID NO:11:

TTGCGGCCGC AA                                                                                                     12